(12) United States Patent
Vayatis et al.

(10) Patent No.: US 11,607,166 B2
(45) Date of Patent: Mar. 21, 2023

(54) MULTIPARAMETER METHOD FOR QUANTIFYING BALANCE

(71) Applicants: CENTRE NATIONAL DE LA RECHERCHE SCIENTIFIQUE, Paris (FR); ÉCOLE NORMALE SUPERIEURE PARIS-SACLAY, Cachan (FR); ETAT FRANCAIS—MINISTERE DE LA DEFENSE—DIRECTION CENTRALE DU SERVICE DE SANTE DES ARMEES, Paris (FR); UNIVERSITE PARIS DESCARTES, Paris (FR)

(72) Inventors: Nicolas Vayatis, Paris (FR); Pierre Paul Vidal, Paris (FR); Nikolaos Promponas Kefalas, Munich (DE); Julien Audiffren, Sceaux (FR); Alain Yelnik, Malakoff (FR); Catherine De Waele Vidal, Paris (FR); Damien Ricard, Clamart (FR)

(73) Assignees: CENTRE NATIONAL DE LA RECHERCHE SCIENTIFIQUE, Paris (FR); ECOLE NORMALE SUPERIEURE PARIS-SACLAY, Cachan (FR); UNIVERSITE PARIS DESCARTES, Paris (FR); ETAT FRANCAIS—MINISTERE DE LA DEFENSE—DIRECTION CENTRALE DU SERVICE DE SANTE DES ARMEES, Paris (FR)

( * ) Notice: Subject to any disclaimer, the term of this patent is extended or adjusted under 35 U.S.C. 154(b) by 629 days.

(21) Appl. No.: 16/346,395

(22) PCT Filed: Nov. 9, 2017

(86) PCT No.: PCT/FR2017/053058
§ 371 (c)(1),
(2) Date: Apr. 30, 2019

(87) PCT Pub. No.: WO2018/087479
PCT Pub. Date: May 17, 2018

(65) Prior Publication Data
US 2020/0187842 A1   Jun. 18, 2020

(30) Foreign Application Priority Data

Nov. 9, 2016  (FR) ........................................ 1660846
Nov. 9, 2016  (FR) ....................................... 1660850

(51) Int. Cl.
*A61B 5/00*   (2006.01)

(52) U.S. Cl.
CPC ................................. *A61B 5/4023* (2013.01)

(58) Field of Classification Search
CPC .............................. A61B 5/4023; G16H 50/30
See application file for complete search history.

(56) References Cited

U.S. PATENT DOCUMENTS 5,388,591 A * 2/1995 De Luca .............. A61B 5/1036
  600/592
2005/0075833 A1* 4/2005 Nashner ............... A61B 5/1036
  702/179

(Continued)

OTHER PUBLICATIONS

R. Gondane and V. S. Devi, "Classification Using Probabilistic Random Forest," 2015 IEEE Symposium Series on Computational Intelligence, 2015, pp. 174-179, doi: 10.1109/SSCI.2015.35. (Year: 2015).*

(Continued)

*Primary Examiner* — Evangeline Barr
(74) *Attorney, Agent, or Firm* — Pearne & Gordon LLP

(57) ABSTRACT

A method for quantifying the balance of an individual recording, on a memory, at least one statokinesigram of the (Continued)

individual obtained from a platform comprising pressure and/or force sensors; extracting, by a processor and from the at least one statokinesigram of the individual recorded on the memory, values of at least one position trajectory parameter of the pressure center and values of at least one stability trajectory parameter of the pressure center; determining, by the processor, the value of a plurality of quantifiers, from the values of the trajectory parameters extracted; comparing, by the processor, said values of the plurality of quantifiers with the values of the same quantifiers obtained from reference statokinesigrams; and determining, by the processor, said value representative of the balance of the individual at the end of the comparison.

24 Claims, 10 Drawing Sheets

(56) References Cited

U.S. PATENT DOCUMENTS

| | | | |
|---|---|---|---|
| 2008/0179110 A1* | 7/2008 | Chai | A61B 5/107 177/25.13 |
| 2014/0081177 A1* | 3/2014 | Eguibar | A61B 5/1036 600/595 |
| 2017/0000387 A1* | 1/2017 | Forth | G06N 7/005 |
| 2017/0296113 A1* | 10/2017 | Cheung | A61B 5/4023 |

OTHER PUBLICATIONS

Shih-Ching Yeh, et al., "Machine learning-based assessment tool for imbalance and vestibular dysfunction with virtual reality rehabilitation system", Apr. 27, 2014, Computer Methods and Programs in Biomedicine, 116 (2014) 311-318 (Year: 2014).*

Examination report issued in counterpart European application No. EP 17801086.4 dated Dec. 23, 2020, 9 pages.

JoséMagalhães de Oliveira, "Statokinesigram normalization method." Behav. Res. 2017, vol. 49. pp. 310-317.

Vayatis, Nicolas. "Digitalisation d'examens cliniques: l'industrialisation necessaire de la recherche en machine learning." Horizon Maths 2015—Santéet données. CMLA, ENS Chachan Dec. 15, 2015. 27 pages.

Baratto, Luigi, et al. "A New Look at Posturographic Analysis in the Clinical Context: Sway-Density Versus other Parametrization Techniques." Motor Control, Jan. 1, 2002. 25 pages.

Paillard, Thierry, et al. "Techniques and Methods for Testing the Postural Function in Healthy and Pathological Subjects." Biomed Research International, vol. 2015. Jan. 1, 2015. 16 pages.

Vayantis, Nicolas. "Digitalisation d'examens cliniques : l'industrialisation nécessaire de la recherche en machine learning par Nicolas Vayatis." Horizon Maths 2015—Santéet données. Une conférence organisee par la Fondation Sciences Mathématiques de Paris et IBM France. Dec. 14 and 15, 2015. Video available at: https://vimeo.com/150655086.

International Search Report and Written Opinion in PCT/FR2017/053058 dated Dec. 19, 2017, 8 pages.

Brieman, Leo "Random Forests." Machine Learning, 45, 5-32, 2001. Kluwer Academic Publishers, The Netherlands. 2001. 28 pages.

Burges, Christopher J.C. "A Tutorial on Support Vector Machines for Pattern Recognition." Bell Laboratories, Lucent Technologies. Kluwer Academic Publishers, Boston. Manufactured in The Netherlands. 1998. 43 pages.

Clark, et al. "Validity and reliability of the Nintendo Wii Balance Board for assessment of standing balance." Centre for Health, Exercise and Sports Medicine, Faculty of Medicine, Dentistry and Health Sciences, The University of Melbourne, Carlton, Victoria 3010, Australia. Nov. 15, 2009. pp. 307-315. 9 pages.

Freund, et al. "Large Margin Classification Using the Perceptron Algorithm." AT&T Labs, Shannon Laboratory. Machine Learning, 37(3):277-296, 1999. 19 pages.

Galar, et al. "A Review on Ensembles for the Class Imbalance Problem: Bagging-, Boosting-, and Hybrid-Based Approaches." IEEE Transactions on Systems, Man, and Cybernetics—Part C: Applications and Reviews. Jun. 23, 2011. 22 pages.

Goble, et al. "Using the Wii Fit as a tool for balance assessment and neurorehabilitation: the first half decade of "Wii-search"." Journal of NeuroEngineering and Rehabilitation 2014, 11:12. Biomed Central LTD. 9 pages.

Rosenblatt, F. "The Perceptron: A Probabilistic Model for Information Storage and Organization in the Brain." Cornell Aeronaturical Laboratory. Psychological Review, vol. 65, No. 6. Apr. 23, 1958. 23 pages.

* cited by examiner

MULTIPARAMETER METHOD FOR QUANTIFYING BALANCE

The present invention relates to the field of the quantification of the balance of an individual. More particularly, the present invention relates to a multiparameter method for quantifying the balance of a person, a device adapted to implement this method and a system integrating said device. The present invention allows, in particular, the evolution of this balance to be tracked, for example in the context of a rehabilitation process, in a self-quantification approach or in the elderly, especially in order to alert on the risks of falling, in a home support approach.

PRIOR ART

Self quantification ("quantified self") is an increasingly common practice and it includes more and more parameters. Similarly, the devices on the market allowing the quantification of different functions related to self-measurement such as sleep or walking are multiplying.

Static and dynamic balances are essential components of our daily movements and a lack of balance is a major cause of falls. In addition, the balance can be modified (namely reduced) as a result of life accidents such as accidents involving the lower limbs, but also in connection with the occurrence of mental disorders or cerebral accidents such as cerebrovascular accidents. This postural instability linked to a disturbance of motor, sensory and/or cognitive functions can promote falling which can be fatal or cause serious decompensation.

According to estimates of the World Health Organization in 2012, nearly 424,000 people worldwide lose their lives each year due to falls, thus placing falls in the second place of accidental death causes in the world. According to the Institut de Veille Sanitaire, there are 450,000 falls each year in France among people over 65 years and it is the most frequent cause of death among the elderly with 4,000 to 4,500 cases per year in France.

People falling is therefore a major public health problem because of its frequency and its medical and social consequences; especially and particularly among the elderly. For example, post-fall syndrome results in a phobia of falling with a loss of self-confidence to perform everyday acts and ultimately leads to grabatization. Thus, many treatments aim to restore the individuals' balance and exercises aim to maintain it.

Despite these challenges, there is currently no intuitive, reliable and inexpensive method or device for quantifying the balance of an individual.

Physicians nowadays appreciate balance through methods for visually tracking the patient, most often through standardized tests such as the Romberg test. The latter can help the physician make a diagnosis and identify the possible causes of a static ataxia. Nevertheless, such tracking allows to qualify and not to objectively quantify the balance of an individual. However, quantitative methods could allow to strengthen the objectivity, the homogeneity of the interpretations, to give the possibility of making comparisons of such tests (e.g. tracking over time or within a group of individuals) and to identify imperceptible behaviors via methods for visually tracking the patient.

Today, there are methods for evaluating the balance that are generally based on the study of the displacement of the pressure center measured from a force platform. In particular, a standardization effort was made in the 1980s and 1990s with the establishment of the "standards 85", including the definition of a protocol comprising placing an individual in a cabin of standardized dimensions, imposing a foot position in order to ensure reproducibility of the parameters with an acquisition time of 51.2 seconds at a sampling frequency of 5 Hz (Gagey et al 1988—Etudes statistiques des mesures faites sur l'homme normal a l'aide de la plate-forme de stabilométrie clinique normalisée).

In this context, the parameters usually determined from the data of displacement of the pressure center, generally at a frequency of 10 Hz minimum, allow to account for the subject's ability to maintain his/her orthostatic balance and can be selected from:
  the length of the displacement,
  the surface of the plot of the statokinesigram corresponding to the surface on which the pressure center moves and is measured in $mm^2$ via the calculation of the surface of the confidence ellipse (based on a Gauss curve) which contains 90% of the support points of the pressure center,
  the length versus the surface (LFS) which corresponds to the ratio between the distance traveled by the pressure center and the surface of the confidence ellipse,
  the variance of the velocity along the Y axis (VFY), or
  the oscillation frequencies.

While posturography is the most appropriate method for evaluating rhe standing position, its place in evaluating balance disorders remains debatable. Several reasons hinder its use: cost of acquisition, of performance, reproducibility of examinations, their sensitivity, their specificity, the difficulties in interpreting the results (large number of measurements to be compared between two states). Indeed, these methods focus on the parameters of the displacement of the pressure center independently and do not combine them. They do not allow to obtain, in the absence of a professional and by a simple and rapid method, a value representative of the balance of the individual.

The force platform called Wii fit balance board (registered trademark) allows to track the displacement of the pressure center and also offers a function for measuring the "Wii fit age" especially based on a measurement of the displacement of the pressure center. Many articles have focused on the evaluation of the balance via this force platform and although it allows to obtain pressure center displacement data similar to those obtained with force platforms based on Wheatstone bridge sensors (Clark et al, 2010—Validity and reliability of Nintendo wii balance board for assessment of standing balance), the measurement of the balance by this type of device is not very conclusive (Goble et al 2014—Using the Wii Fit as a tool for balance assessment and neurorehabilitation: the first half decade of "Wii-search").

This lack of performance or at best this reduced performance is probably linked to the single-factor appreciation of the displacement of the pressure center and to random changes in the acquisition frequency over time that may lead to over- or under-acquisition. On the rare occasions that multiparameter methods are used, the latter are not able to produce satisfactory results because the data to be studied are very complex and difficult to model. Thus, the analytical methods previously used to assess balance do not provide a unique and reliable value that can be easily measured using a simple and inexpensive device.

This was confirmed, in particular, by an oral presentation at the Horizon Maths 2015 conference held on 14 and 15 Dec. 2015 (URL: https://www.sciencesmaths-paris.fr/upload/Contenu/HorizonMaths/HM2015/hm2015-vayat-is.pdf). During this oral presentation, presented as a sharing of scientific reflection and issues, the speaker mentioned the techniques used in the state of the art and mentioned 4 to 5 reference indicators. He notes the need for synthetic indicators that cannot be summarized by the five reference characteristics in posturography and mentions the existence of 1,000 descriptors, associated for example with the mechanical, geometric and frequency aspects.

There is therefore a need for a balance quantification device that can be used routinely by anyone who wants to monitor their balance and at a low cost, but also by public authorities or health personnel.

Technical Problem

The invention aims to overcome the disadvantages of the prior art. In particular, the invention aims to provide a reliable method for quantifying the balance, that is to say for establishing a value representative of the balance state of the individual, that is rapid, simple, and does not necessarily require the intervention of a specialist in the posturology field. It should be noted that this method is not intended to replace the general practitioner or specialist and does not make a diagnosis.

The invention also aims to provide a balance quantification device that can be integrated into a complete balance quantification system.

BRIEF DESCRIPTION OF THE INVENTION

To this end, the invention relates to a method for quantifying the balance of an individual in order to obtain a value representative of the balance of said individual, said method being implemented by a device comprising at least one data processing module connected to a storage means and, possibly a classification module, said method comprising:
  a) a step of recording, on the storage means, at least one statokinesigram of the individual obtained from a platform comprising pressure and/or force sensors, and optionally body mass index (BMI) data of said individual,
  b) a step of extracting, by the data processing module and from the one or more statokinesigram(s) of the individual recorded on the storage means, values of at least one position trajectory parameter of the pressure center and values of at least one stability trajectory parameter of the pressure center,
  c) a step of determining, by the data processing module, the value of several quantifiers, from the values of the trajectory parameters extracted in step b),
  d) a step of comparing, by the data processing module, said values of several quantifiers with the values of the same quantifiers obtained from reference statokinesigrams, and
  e) a step of determining by the data processing module, said value representative of the balance of the individual at the end of the comparison.

The implementation of this method includes determining several quantifiers which are then jointly processed in a step of comparing and determining a value representative of the balance. Unlike the prior art, the method according to the invention comprises taking into account and combining trajectory parameters linked to the position and to the stability of the pressure center in order to obtain a value representative of the balance.

According to Other Optional Features of the Method:
  said device implementing the method further comprises a classification module and the recording step further comprises recording body mass index (BMI) data of said individual, and is followed by a step of classifying, by said classification module, the one or more statokinesigram(s) of the individual in a BMI category depending on the recorded BMI data, said classification step preferably takes place after the recording step a) and before the extraction step b). In addition, during the step of comparing said values of at least two quantifiers, said values of at least two quantifiers are compared with the values of the same quantifiers obtained from reference statokinesigrams classified in the same BMI category as the BMI category determined during the classification step. Taking this into account and combining the BMI and a quantifier in order to obtain a value representative of the balance allows to improve the results of the quantification of the balance.
  the BMI category determined in the classification step is selected from at least three BMI categories. Defining at least three BMI categories allows to improve the relevance of the value representative of the balance obtained by the method according to the invention. The BMI categories are: BMI of less than 21, BMI between 21 and 30, and BMI greater than 30.
  step b) further comprises extracting the values of at least one dynamics trajectory parameter of the pressure center. Taking into account the values of a dynamics trajectory parameter of the pressure center allows to improve the relevance of the representative value obtained as can be shown by the curves of the ROC (Receiver Operating Characteristic) curves and more particularly the area under the curve (AUC) data.
  at least one position trajectory parameter of the pressure center is selected from: the position of the pressure center along the X axis, the position of the pressure center along the Y axis and the radius in polar coordinates. These position trajectory parameters of the pressure center were selected by the inventors from a multitude of position trajectory parameters because they are particularly relevant for balance quantification. Preferably, at least one position trajectory parameter of the pressure center is the radius in polar coordinates.
  at least one stability trajectory parameter of the pressure center is selected from: the radial balance, the time balance and the ballistic interval. These stability trajectory parameters of the pressure center were selected by the inventors from a multitude of stability trajectory parameters because they are particularly relevant for balance quantification.
  at least one dynamics trajectory parameter of the pressure center is selected from: the velocity of the displacement of the pressure center, the acceleration of the displacement of the pressure center, the power and the deviation. These dynamics trajectory parameters of the pressure center were selected by the inventors from a multitude of dynamics trajectory parameters because they are particularly relevant for balance quantification.
  at least one of the quantifiers determined in step c) is selected from: the mean value, the median value, the variance value, and an extreme value, of said trajectory parameter. Alternatively, at least one of the quantifiers determined in step c) is selected from: the mean value, the median value, the variance value, the mean square value and an extreme value, of said trajectory parameter.
  step b) is performed from two statokinesigrams generated during a Romberg test. The Romberg test is a test used by many posturology professionals for decades and it allows to obtain a value representative of the balance in the context of the invention, especially by comparing the values of the statokinesigrams obtained with the eyes closed or with the eyes open.

at least one of the quantifiers determined in step c) is an extreme value of said trajectory parameter, said extreme value corresponding to a percentile between a percentile greater than or equal to 5 and a percentile of less than or equal to 15, or to a percentile between a percentile greater than or equal to 85 and between a percentile of less than or equal to 95, of the trajectory parameter values. The analysis of the extreme values, which is generally not found in current methods for analyzing the balance, allows to generate results that are particularly relevant in the context of the invention.

steps d) and e) are performed by implementing the values of the quantifiers determined in step c) in a scoring algorithm previously calibrated based on the values of the same quantifiers obtained from the reference statokinesigrams, preferably classified in the same BMI category as the BMI category determined in step a). Using a scoring algorithm integrating steps d) and e) allows, in particular, to shorten the implementation time of the method and to improve the efficiency of the method.

the previously calibrated scoring algorithm was obtained by implementing a supervised learning statistical method, preferably a RANKING FOREST or RANDOM FOREST method. The inventors discovered that, in the context of balance quantification, the RANKING FOREST or RANDOM FOREST methods are very effective. Preferably, the supervised learning statistical method is used in combination with a Bagging step. Thus, the previously calibrated scoring algorithm may be obtained by implementing a supervised learning statistical method comprising implementing a Bagging step.

The method comprises, in step c), determining the value of at least five quantifiers. Prior art methods are generally based on a one-to-one comparison of values extracted from the statokinesigrams, whereas in the context of the invention, combining at least five quantifiers allows better performance.

The invention further relates to a device for quantifying the balance of an individual, said device comprising:

a communication module able to receive data comprising at least one statokinesigram of said individual and advantageously body mass index data of said individual, a storage means able to record the statokinesigram and, where applicable, the BMI data, and at least one data processing module able to connect to the storage means, said data processing module being configured to:

Extract, from a statokinesigram of said individual transmitted by the communication module, values of at least one position trajectory parameter of the pressure center and values of at least one stability trajectory parameter of the pressure center, Determine several quantifiers, from the values of the extracted trajectory parameters, Compare the values of said quantifiers with the values of the same quantifiers obtained from reference statokinesigrams, and Determine a value representative of the balance of the individual based on said comparison.

Advantageously it further comprises a classification module configured to classify a statokinesigram of the individual in a body mass index (BMI) category depending on the BMI of said individual, and compare the values of said quantifiers with the values of the same quantifiers obtained from reference statokinesigrams classified in the same BMI category as the BMI category of the statokinesigram of the individual. Thus, the invention also relates to a device for quantifying the balance of an individual comprising a classification module and where:

The communication module is further able to receive BMI data from said individual, The storage means is further able to record the BMI data, The classification module is configured to classify a statokinesigram of the individual in a BMI category depending on the BMI data of said individual, and The data processing module is further configured to compare the values of said quantifiers with the values of the same quantifiers obtained from reference statokinesigrams classified in the same BMI category as the BMI category of the statokinesigram of the individual.

The invention further relates to a system for quantifying the balance of an individual, comprising:

a platform, said platform being adapted to receive an individual and comprising pressure and/or force sensors configured to generate raw data, at a first frequency, as a function of a pressure exerted by the feet of the individual on the platform, a raw data processing unit, arranged to obtain at least one statokinesigram of the individual from the raw data generated by the platform, and a balance quantification device according to the invention, able to communicate with the processing unit.

According to other optional features of the system:

the platform is configured to measure the values of its different sensors at a frequency greater than or equal to 25 Hz. This allows to increase the reliability of the calculated representative values.

the quantification device further comprises a re-sampling module, said re-sampling module being configured to process the raw data or the statokinesigrams at a first frequency so as to generate statokinesigrams re-sampled at a second frequency, said second frequency having a substantially constant frequency. This allows to increase the reliability of the calculated representative values.

Other advantages and characteristics of the invention will appear upon reading the following description given by way of illustrative and non-limiting example, with reference to the appended Figures which represent:

Figure 2:
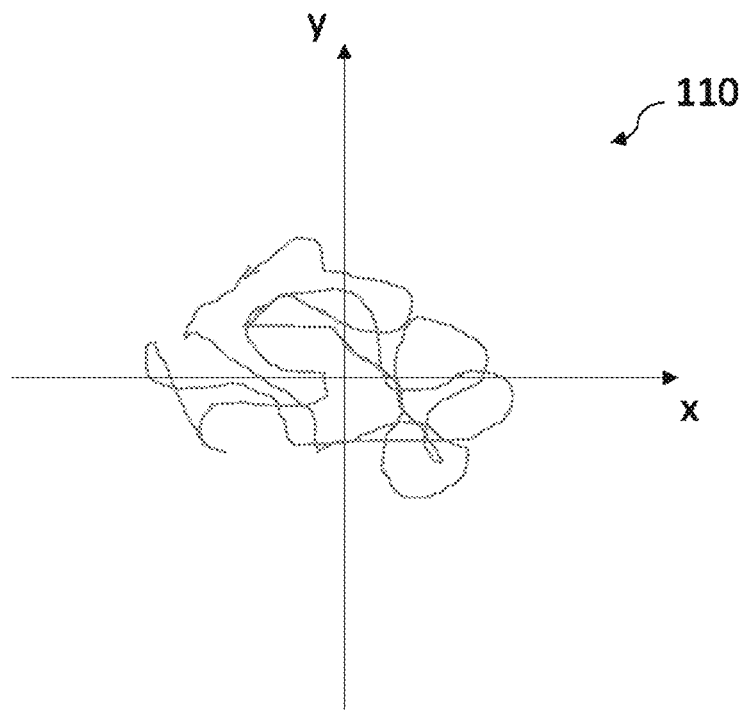
FIG. 2 shows a statokinesigram according to the invention where the axis y corresponds to the anterior-posterior axis and the x axis to the medial-lateral axis.
Figure 3A:
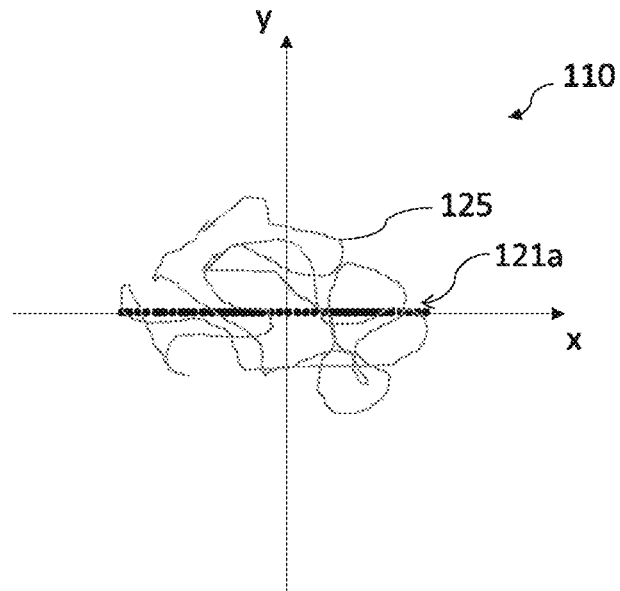
Figure 3B:
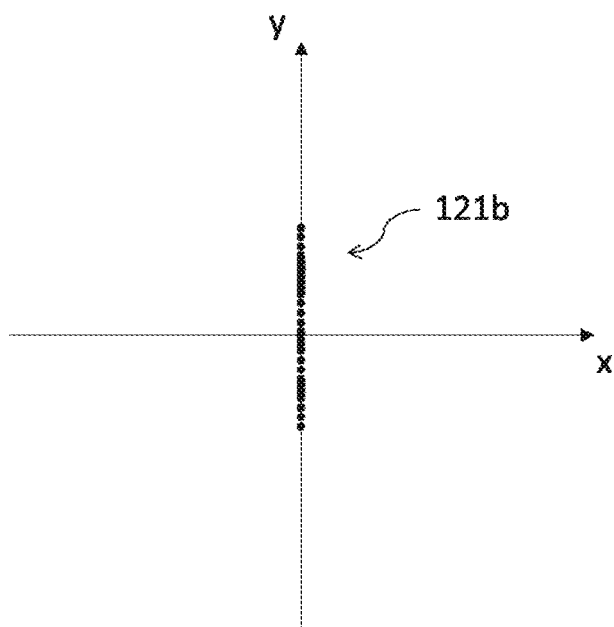
Figure 4:
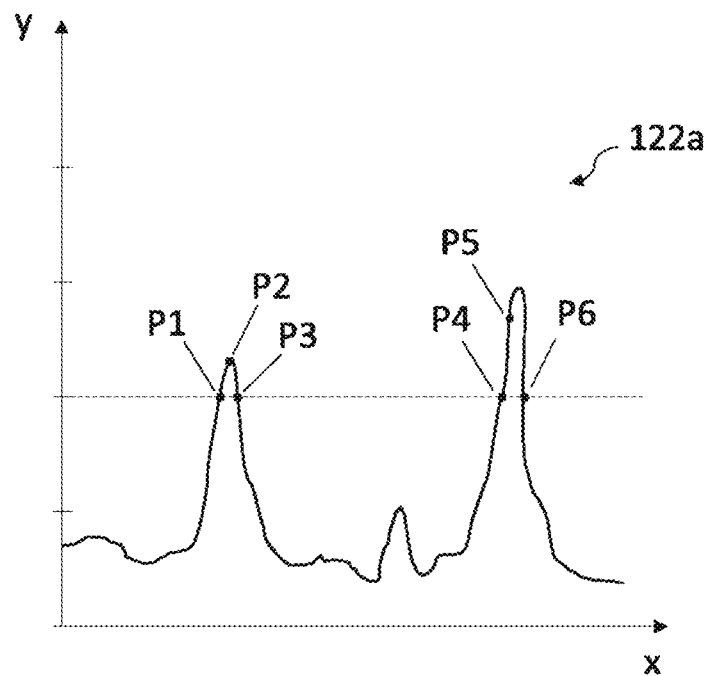

FIGS. 3A and 3B show a statokinesigram according to the invention, with FIG. 3A corresponding to the projection on the X axis of all the values of the "position of the pressure center along the X axis" parameter and FIG. 3B representing the projection on the Y axis of all the values of the "position of the pressure center along the Y axis" parameter FIG. 4 shows all the values as a function of time (X axis) of the "time balance" parameter calculated based on the statokinesigram shown in FIG. 2. The dotted line showing a threshold value for calculating the ballistic interval parameter according to the invention.

Figure 5:
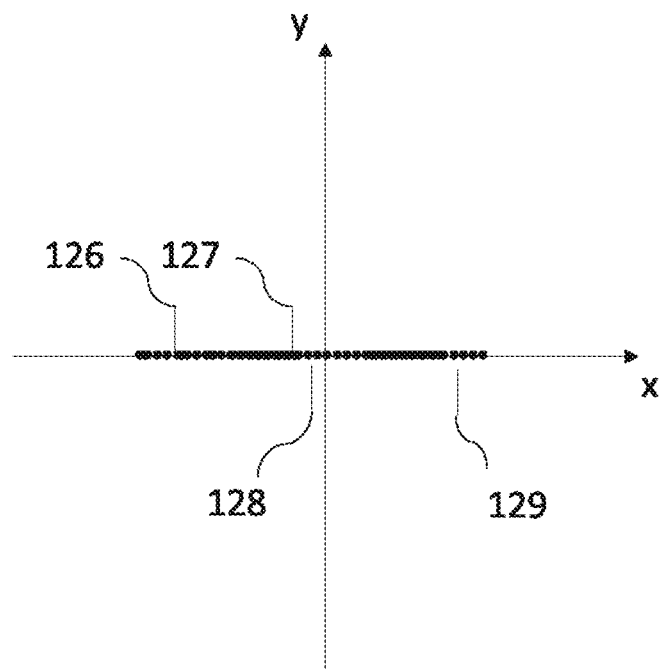

FIG. 5 shows the projection on the X axis of all the values of the "position of the pressure center along the X axis" parameter, as well as four quantifiers calculated from this parameter.

Figure 6:
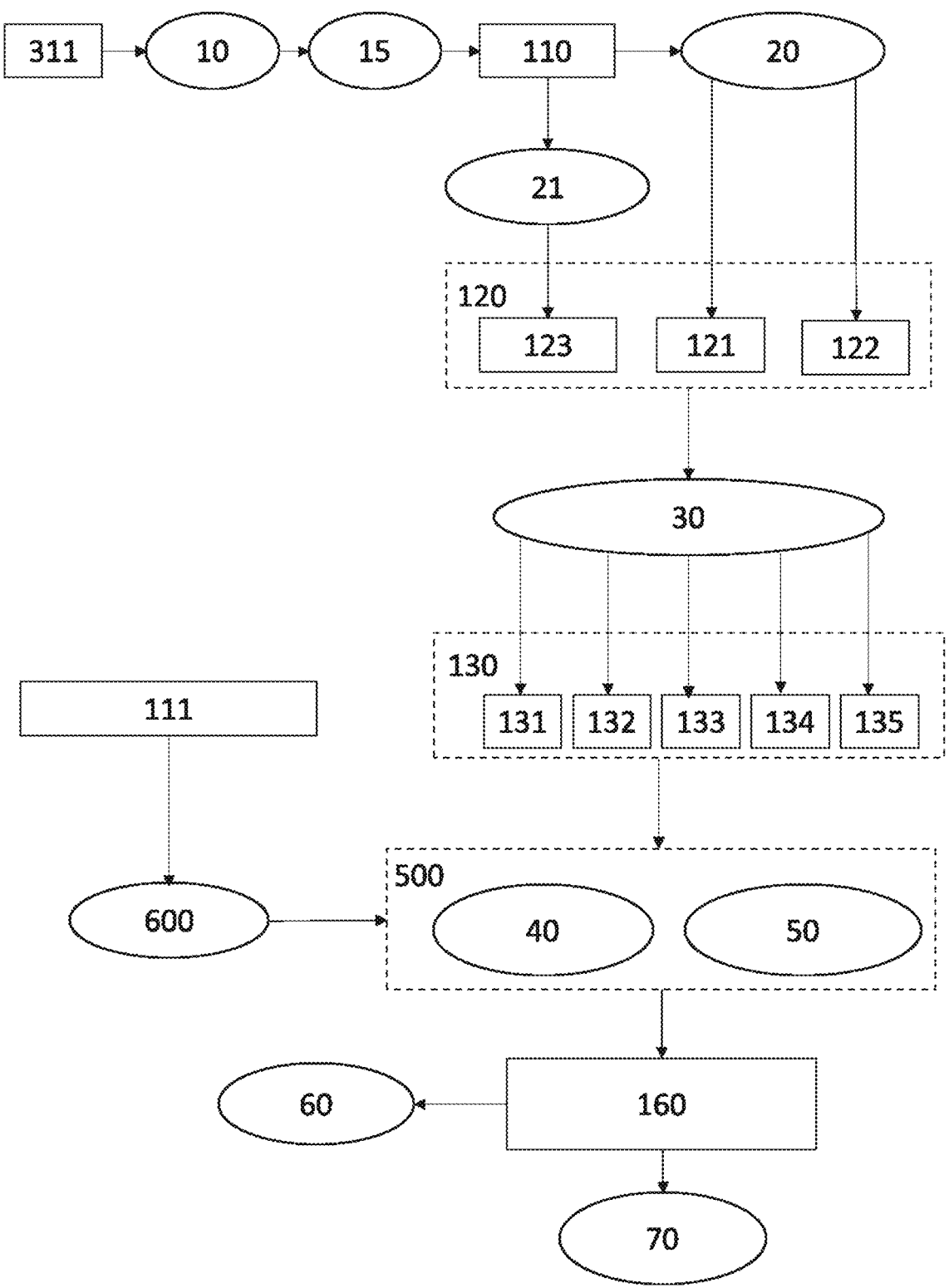

FIG. 6 shows an example of the implementation of the balance quantification method according to the invention. The numbers arranged in oval shapes correspond to method steps while those arranged in rectangles correspond to values obtained after implementing these steps.

Figure 7A:
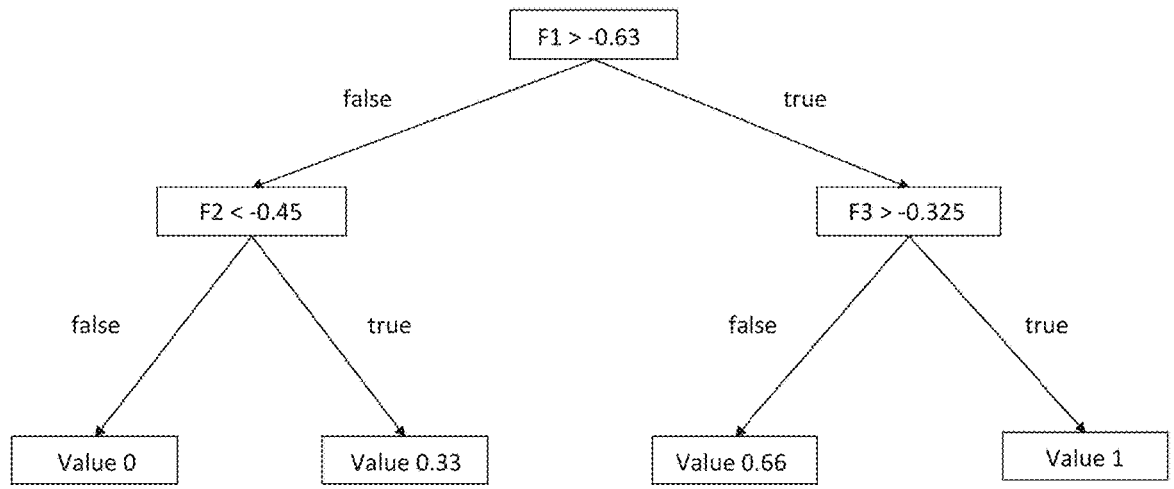
Figure 7B:
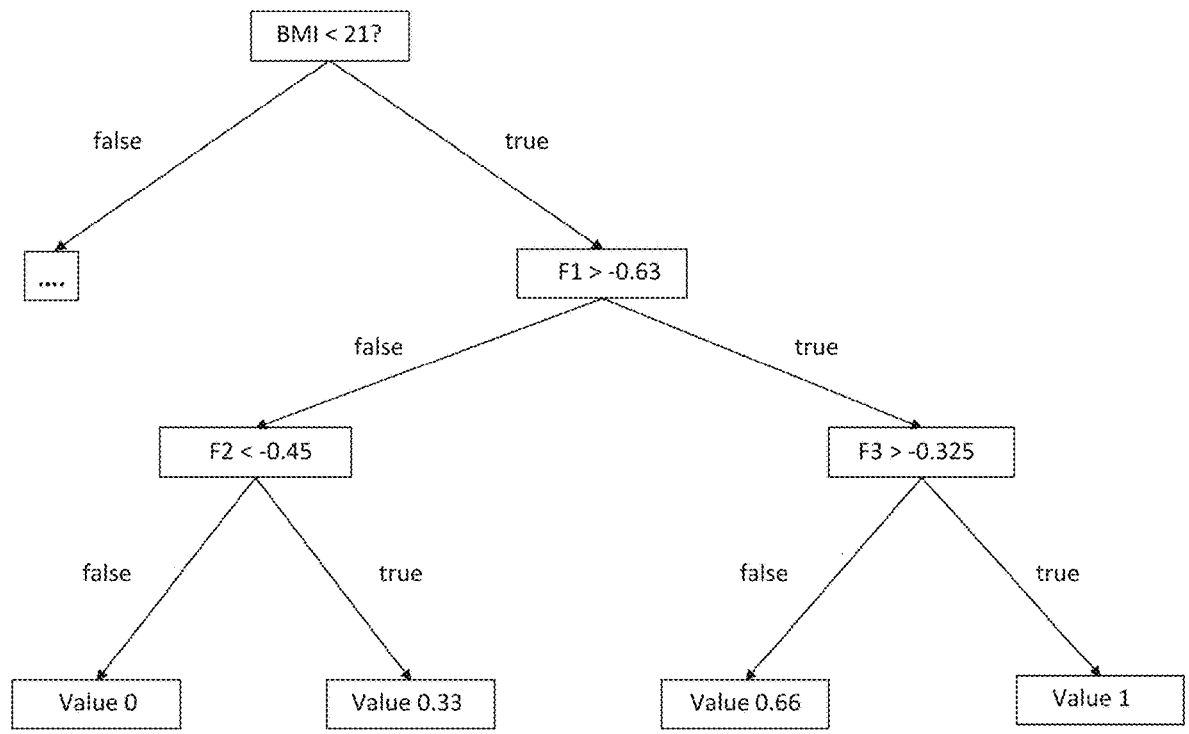

FIGS. 7A and 7B show two decision trees built from a Ranking Forest type algorithm according to two embodiments of the invention, with FIG. 7B including a preliminary step of classifying depending on the BMI. F1 corresponds to the ratio eyes closed/eyes open for the 90 percentile of the ballistic interval, F2 is the ratio eyes closed/eyes open for the variance of the position on the Y axis and F3 is the variance of the time balance with the eyes closed.

Figure 8:
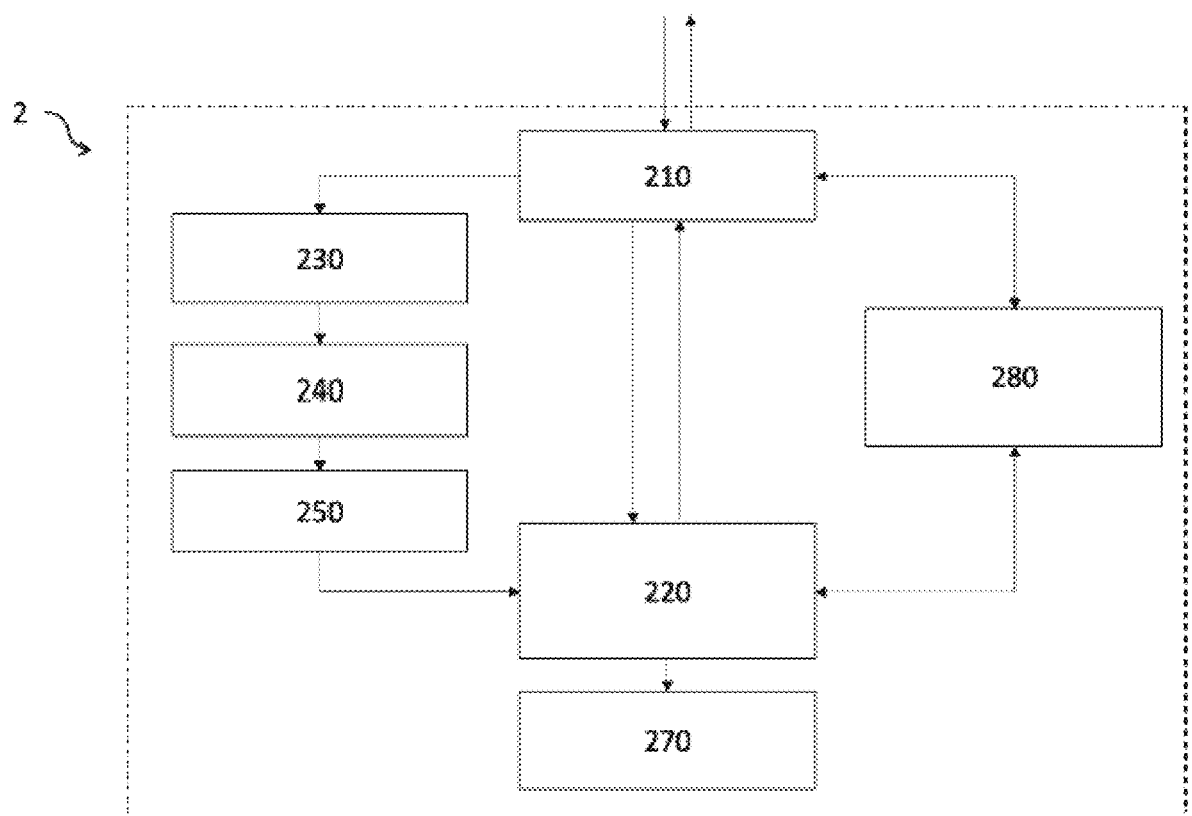

FIG. 8 shows a balance quantification device according to the invention.

Figure 9:
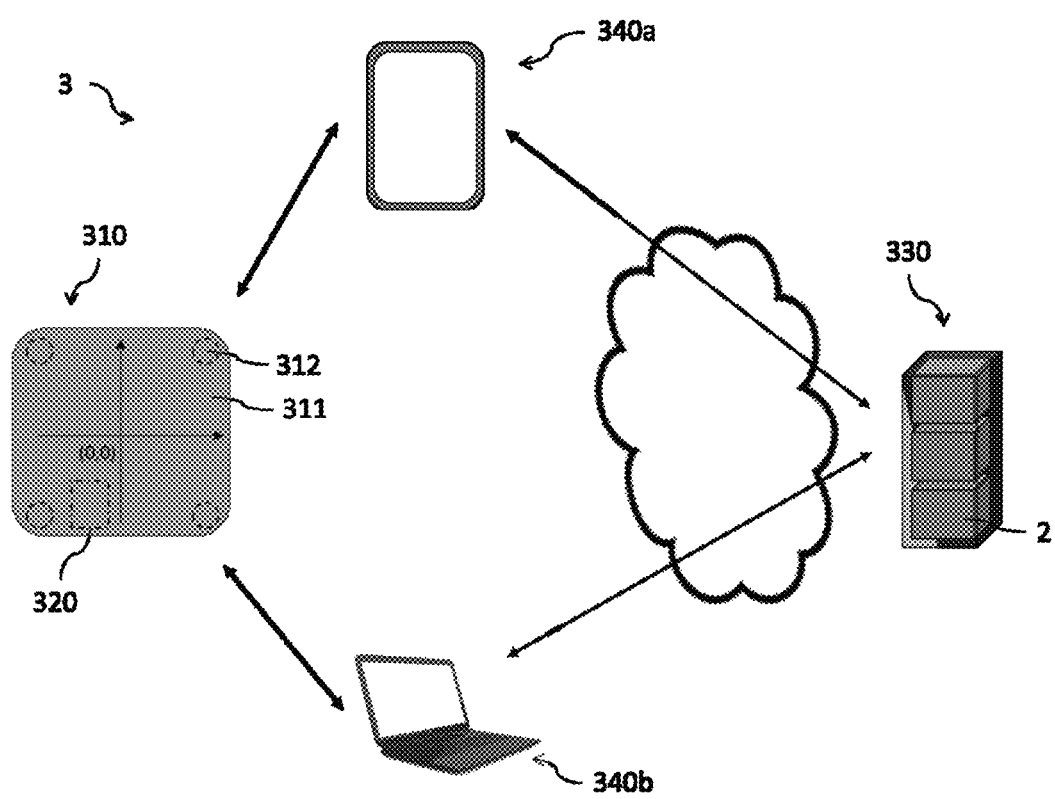

FIG. 9 shows a balance quantification system according to the invention.

Figure 10:
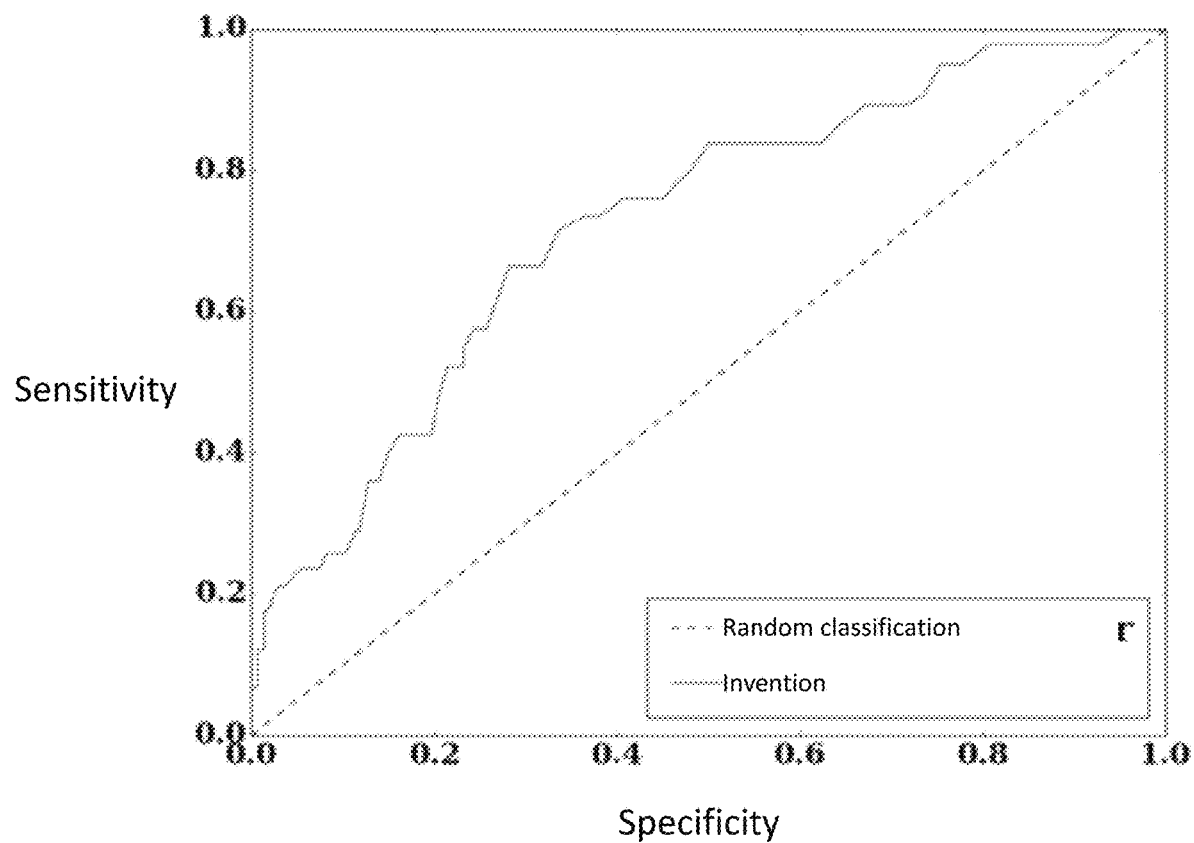

FIG. 10 shows the ROC curve of the score obtained and built from a Ranking Forest type algorithm according to an embodiment of the invention.

DESCRIPTION OF THE INVENTION

In the following description, the "balance", within meaning of the invention, corresponds to the postural balance linked to the stability of the body and more particularly to the stability the center of gravity of an individual. The notion of balance according to the invention is linked to the ability of an individual to avoid falling and encompasses static balance and dynamic balance.

The "balance quantification" corresponds, within the meaning of the invention, to the assignment of a value, for example a score, a classification or a grade, to a trajectory or a displacement of the pressure center of an individual. This balance quantification allows to obtain a value representative of the balance and can be performed based on many linear or non-linear scales of different sizes (e.g. 1, 5, 10, 100). The balance representative value assigned when quantifying the balance can also allow to assign an individual to a group, for example via a decision rule. The quantification according to the invention can be performed, in particular, by implementing a scoring algorithm generated from a learning method.

The "body mass index" (BMI) corresponds, within the meaning of the invention, to a value for estimating the body size of a person. In the following, body mass index data or body mass index will be referred to interchangeably. This body mass index is generally expressed in kilograms.metres$^{-2}$ (kg.m$^{-2}$) and is calculated based on the following formula:

$$BMI = mass/size^2$$

Thus, a "BMI category" corresponds, within the meaning of the invention, to a group of values derived from a BMI classification. In the following, BMI category data or BMI category will be referred to interchangeably. Many classifications have been proposed. For example, the WHO proposes the following classification:
<18.5 underweight
18.5 to 24.99 normal weight
25 to 29.99 overweight
≥30 obesity By "model" or "rule" or "scoring algorithm" must be understood, within the meaning of the invention, a finite series of operations or instructions allowing to quantify the balance, that is to say to classify one or more individuals within previously defined groups Y, or to rank one or more individuals within a classification. Implementing this finite sequence of operations allows, for example, to assign a label $Y_0$ to an observation described by a set of characteristics $X_0$ using, for example, the implementation of a function f likely to reproduce Y, having observed X.

$$Y = f(X) + e$$

where e symbolizes the noise or measurement error.

By "supervised learning method" is meant, within the meaning of the invention, a method for defining a function f from a base of n labeled observations $(X_{1...n}, Y_{1...n})$ where $Y = f(X) + e$.

Within the meaning of the invention, by "pressure center" is meant, the projection on the horizontal plane passing through the point of contact between the subject and the ground of the barycenter of the vertical forces exerted on the ground by the body of the subject. These measurements can be made using a platform analyzing the distribution of the pressures under the foot bed such as a force platform or a shoe or a deformable ground (Benda, B. J. et al 1994. Biomechanical relationship between center of gravity and center of pressure during standing. Rehabilitation Engineering, IEEE Transactions on 1994, 2, 3-10). Without being an exact projection of the center of gravity, the pressure center is strongly linked to the center of gravity. The displacement of the pressure center is generally faster and wider than that of the center of gravity in order to keep it in balance. It reflects the efforts made by an individual to control the position of his/her center of gravity.

Within the meaning of the invention, by "center of gravity" is meant, the center of gravity of the body of an individual. It corresponds, within the meaning of the invention, to the barycenter of the masses of the individual. The center of gravity cannot be maintained in perfect stability and, for example, when standing upright, the center of gravity oscillates from front to back and from left to right.

By "statokinesigram" or "trajectory of the pressure center", are meant the data related to the trajectory or displacement of the pressure center. The statokinesigram can also be called a stabilogram and is usually generated via a platform such as a force platform, an "intelligent" floor equipped with sensors or soles equipped with pressure sensors. It corresponds to the calculated trajectory of the pressure center over time. The trajectory of the pressure center is defined by a set of position data in an orthonormal reference frame x,y as a function of time and over a defined period of time.

The "platform", within the meaning of the invention, corresponds to a device resting on the ground including sensors, for example of the force or pressure sensor type, producing an electrical, optical or magnetic signal proportional to the force applied on said platform by the feet of an individual. The sensors used can be, for example, Wheatstone bridge strain gauges in order to generate the 3 force and moment components Fx, Fy, Fz, Mx, My and Mz; piezoelectric pressure sensors, piezoresistive pressure sensors or capacitive pressure sensors. Within the meaning of the invention, the platform is configured to generate "raw data" derived from said sensors.

By "parameter" and more particularly by "parameter calculated from the trajectory of the pressure center", is meant, within the meaning of the invention, a transformation of the trajectory of the pressure center into a set of values.

A trajectory parameter related to the position of the pressure center can also be called a position trajectory parameter of the pressure center, a trajectory parameter linked or related to the stability of the pressure center can also be called a stability trajectory parameter of the pressure center and a trajectory parameter linked or related to the dynamics of the pressure center can also be called a dynamics trajectory parameter of the pressure center. These parameters are more particularly described in the following description.

By "quantifier" and more particularly by "quantifier calculated from a transformation of an obtained parameter", is meant, within the meaning of the invention, a single value obtained by selecting or transforming all the values of a parameter.

By "reference quantifier" is meant, a value obtained from a reference statokinesigram from a person whose balance was previously qualified.

Within the meaning of the invention, the "ROC (Receiver Operating Characteristic) curve" represents the evolution of the sensitivity (true positive rate) as a function of the specificity (false positive rate) of a model for each given threshold value. It is a curve rising between the point (0,0) and the point (1,1) and is normally located above the first bisector. Indeed, a random prediction would give a line corresponding to the first bisector. For an ROC curve, the higher the curve is above the first bisector, the better the prediction and the area under the ROC curve (AUC—Area Under the Curve) is indicative of the quality of the model (1 for an ideal prediction, 0.5 for a random prediction).

In the following description, the same references are used to designate the same elements.

According to a first aspect, the invention relates to a method 1 for quantifying the balance of an individual to obtain a value representative of the balance of said individual. Whereas, until now, recognized methods have been based on visual assessments or observations and are not completely objective, the method according to the present invention has the advantage of generating a value also designated by a score, and more particularly a numerical value. In addition, this value can be generated completely automatically, objectively and without the need to provide the method with information about the individual in addition to one or more statokinesigram(s).

Figure 1A:
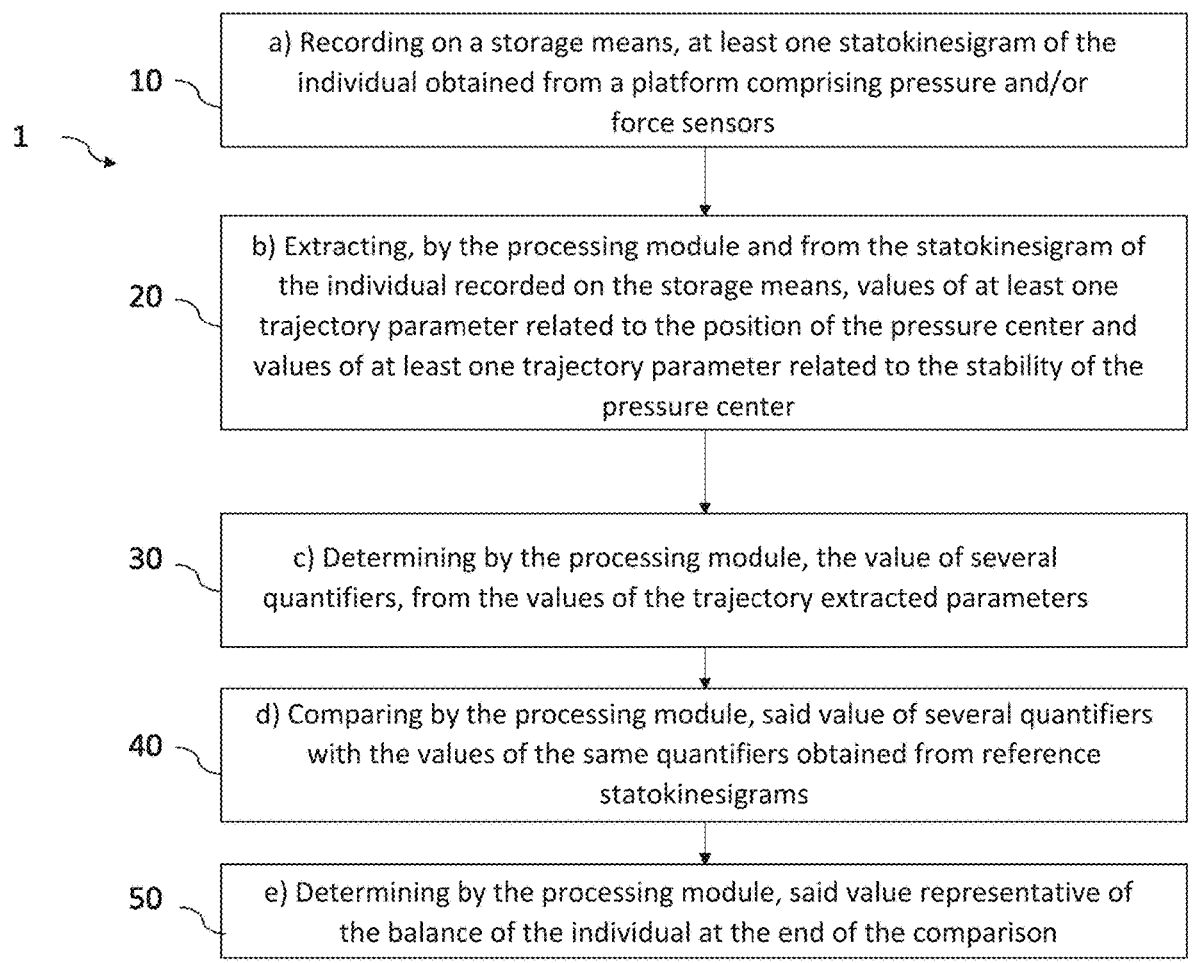
FIGS. 1A and 1B show diagrams of the balance quantification method according to two embodiments of the invention.

An embodiment of this quantification method 1, shown in FIG. 1A, is implemented by a device with at least one data processing module 220 connected to a storage means 280. Advantageously, the device can be the quantification device 2 according to the invention.

More particularly, as shown in FIG. 1A, the quantification method 1 according to the invention comprises:
a) a step of recording 10, on the storage means 280, at least one statokinesigram 110 of the individual obtained from a platform 310 comprising pressure and/or force sensors 312,
b) a step of extracting 20, by the data processing module 220 and from the statokinesigram 110 of the individual recorded on the storage means 280, values of at least one trajectory parameter related to the position 121 of the pressure center and values of at least one trajectory parameter related to the stability 122 of the pressure center,
c) a step of determining 30, by the data processing module 220, the value of several, for example at least two, quantifiers 130, from the values of the trajectory parameters 121, 122 extracted in step b),
d) a step of comparing 40, by the data processing module 220, said values of several quantifiers 130 with the values of the same quantifiers obtained from reference statokinesigrams 111, and
e) a step of determining 50, by the data processing module 220, said value 160 representative of the balance of the individual at the end of the comparison 40.

Figure 1B:
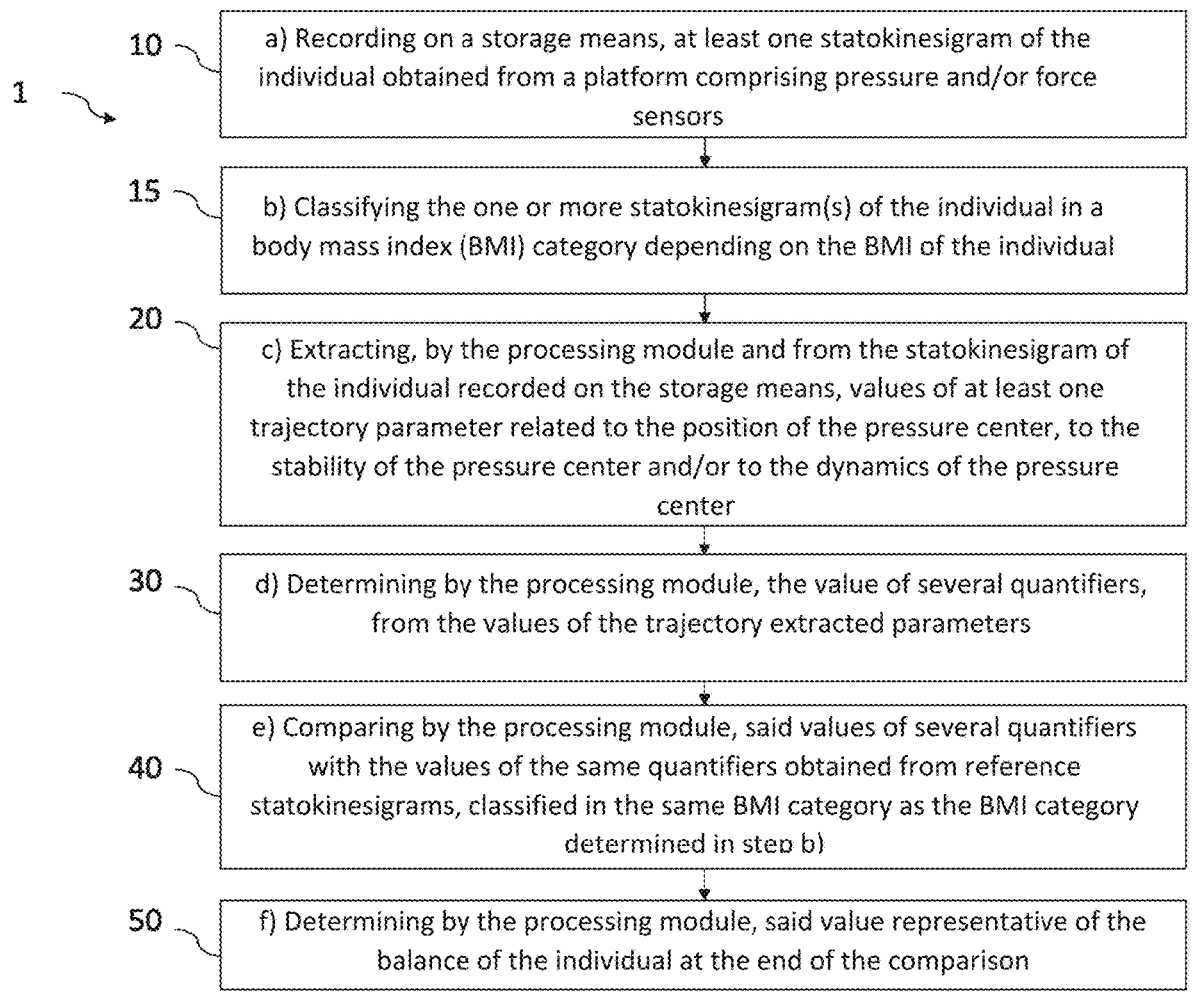

The quantification method 1, shown in FIG. 1B, is implemented by a device comprising at least one data processing module 220 connected to a storage means 280 and a classification module 250. Advantageously, the device can be the quantification device 2 according to the invention.

More particularly, as shown in FIG. 1B, the quantification method 1 according to the invention comprises:
a) a step of recording 10, on the storage means 280, at least one statokinesigram 110 of the individual obtained from a platform 310 comprising pressure and/or force sensors 312 and BMI data 16 of said individual,
b) a step for classifying 15, by the classification module 250, the one or more statokinesigram(s) 110 of the individual in a BMI category 150 depending on the BMI 16, of the individual,
c) a step of extracting 20, by the data processing module 220 and from the statokinesigram 110 of the individual recorded on the storage means 280, values of at least one trajectory parameter related to the position 121 of the pressure center, to the stability 122 of the pressure center and/or to the dynamics 123 of the pressure center,
d) a step of determining 30, by the data processing module 220, the value of several quantifiers 130, from the values of the trajectory parameters 121, 122, 123 extracted in step c),
e) a step of comparing 40, by the data processing module 220, said values of several quantifiers 130 with the values of the same quantifiers obtained from reference statokinesigrams 111 classified in the same BMI category as the BMI category determined in step b), and
f) a step of determining 50, by the data processing module 220, said value 160 representative of the balance of the individual at the end of the comparison 40.

The balance quantification method 1 according to the invention is based on processing the trajectory data of the pressure center of an individual such as transcribed in a statokinesigram 110.

These trajectory data of the pressure center of an individual generally correspond to the trajectory data of the pressure center and are generally acquired when the individual is standing up.

Preferably, the acquisition is done standing up, for example with the feet together or at the hips.

The influence of visual afferents on stability is measured by generating two displacement or trajectory kinetics of the pressure center, one with the eyes open and the other with the eyes closed. Thus, preferably, the extraction step 20 is performed from a statokinesigram 110 obtained while the individual has his/her eyes open and a statokinesigram 110 obtained while the individual has his/her eyes closed.

In particular, the acquisition time of a statokinesigram 110 can be between 5 and 70 seconds, preferably between 20 and 60 seconds and even more preferably between 20 and 40 seconds.

Advantageously, the trajectory data of the pressure center can be obtained during a Romberg test. The Romberg test consists of placing the individual standing up, motionless, arms along the body, looking straight ahead. The displacement of the pressure center is recorded for 30 seconds. For example, a 30 second recording is made with the eyes open and another 30 second recording is made with the eyes closed.

Alternatively, it is possible to increase the sensitivity of the method by using a foam placed on a support and able to deform or disturb the proprioceptive and tactile information. This foam can, for example, have a thickness of 1 to 10 millimeters and a density between 100 and 500 kg/m$^3$.

The method according to the invention can be implemented from the data related to the displacement of the pressure center, that is to say based on at least one statokinesigram 110 or based on the raw data derived from the sensors and related to the displacement of the pressure center.

The quantification method 1 according to the invention comprises a step of recording 10 at least one statokinesigram 110 of the individual and, advantageously, BMI data 16 on a storage means 280. This recording can be performed on all types of memory such as transient or non-transient memories. This recording is preferably made on a non-transient memory.

The statokinesigram 110 can be generated well before the method according to the invention is implemented and at a remote location. Alternatively, the statokinesigram 110 can be generated just before the balance quantification method 1 according to the invention is implemented and by a same system. Thus, the quantification method 1 according to the invention may include a step of generating the raw data related to the displacement of the pressure center 11 beforehand. This step is nevertheless optional and can be performed before the quantification method 1 according to the invention by known devices and methods. The raw data related to the displacement of the pressure center correspond, for example, to the pressure values measured by each of the sensors present on the platform.

These raw data can be subject to a step of transforming 12 into trajectory data of the pressure center (namely a statokinesigram). This transformation step is also optional because it can be performed before the method according to the invention by known methods. FIG. 2 is a graphical representation of a statokinesigram 110 according to the invention and more particularly of the plot 125 of the statokinesigram 110.

The quantification method 1 according to the invention may advantageously comprise a step of classifying 15 the one or more statokinesigram(s) 110 of the individual in a body mass index (BMI) category 150 depending on the BMI 16 of the individual. This classification step can be performed by a classification module 250 in connection with the statokinesigram 110 of the individual recorded on a storage means 280 and from a BMI value 16 associated with the individual that can also be recorded on the storage means 280. This step 15 may, for example, comprise assigning a label to the statokinesigram of the individual, this label being a function of the BMI value of said individual. The BMI value of the individual can be generated well before the method according to the invention is implemented and at a remote location. Alternatively, the BMI value 16 can be generated just before the balance quantification method 1 according to the invention is implemented and by a same system. Thus, the quantification method 1 according to the invention may include a step of generating the BMI data 16 of the individual beforehand. This step is nevertheless optional and, as mentioned, can be performed before the quantification method 1 according to the invention by known devices and methods. The classification according to step 15 may allow the one or more statokinesigram(s) 110 to be classified in at least two categories 150, preferably at least three categories 150. For example, the BMI categories 150 can be:

BMI of less than 21,
BMI between 21 and 30, and
BMI greater than 30.

The quantification method 1 according to the invention comprises a step of extracting 20 values of several trajectory parameters 120 from a statokinesigram 110 of the individual. This extraction step can be performed by a data processing module 220 from the statokinesigram 110 of the individual recorded on a storage means 280.

This extraction step 20 allows the transformation of the trajectory data of the pressure center (namely a statokinesigram), in order to obtain parameters that transcribe the properties of this displacement of the pressure center. The thus calculated parameters are, for example, for each of the times t, the speed, the acceleration, the position on an axis of the pressure center.

This extraction step 20 can be performed from a set of data related to the displacements of the pressure center such as the trajectory data of the pressure center or the raw data of the force platform. Indeed, alternatively, the extraction or calculation of the parameters according to the invention can be directly performed from the raw data of the sensors in a single step including generating the trajectory data 12 of the pressure center and then transforming into parameters 120.

The inventors discovered that, in order to obtain a reliable quantification of the balance of an individual, a multiparameter method combining the analysis of several parameters from different parameter families was essential.

As part of the implementation of the method according to the invention, the inventors classified these transformations performed during the extraction step 20 in three categories:
i) those associated with the position of the pressure center,
ii) those associated with the stability of the pressure center, and iii) those associated with the dynamics of the displacement of the pressure center.

Thus, the extraction step 20, by the data processing module 220 and from the statokinesigram 110 of the individual, may comprise extracting 20 the values of at least one, preferably at least two trajectory parameters 120 related to:
the position 121 of the pressure center,
the stability 122 of the pressure center, and/or
the dynamics 123 of the pressure center.

In addition, from many trajectory parameters, the inventors selected the trajectory parameters most effective for quantifying the balance. They determined that using at least one trajectory parameter related to the position 121 of the pressure center and at least one trajectory parameter related to stability 122 of the pressure center. Thus, the trajectory parameters calculated as part of the quantification method 1 according to the invention comprise:
at least one parameter related to the position 121 of the pressure center, and
at least one parameter related to the stability 122 of the pressure center.

Indeed, the inventors determined that using at least one parameter of these two classes allowed to increase the accuracy of the quantification and thus to obtain significantly better performances, both compared to the literature but also compared to the scoring algorithms according to the invention using the literature descriptors.

In addition, the inventors also showed that adding a parameter related to the dynamics 123 of the pressure center, to the stability and position parameters of the pressure center, could allow to improve the quantification. Thus, according to the invention, the calculated trajectory parameters can also comprise at least one parameter related to the dynamics 123 of the pressure center.

Transformations Associated with the Position 121 of the Pressure Center,

The Position of the Pressure Center Along the X Axis

This position corresponds to the position of the pressure center compared to the median line of the orthonormal reference frame in a plan of the X axis. For example, in the case of a position of the pressure center shifted towards the left at a time t, the position along the X axis has, for this time t, a negative value indicating a left hyper-support. This position can be measured, for example, in millimeters. FIG. 3A shows a set of values of the "position of the pressure center along the X axis" parameter 121a obtained from the statokinesigram 110 shown in FIG. 2.

The Position of the Pressure Center Along the Y Axis

This position corresponds to the position of the pressure center with respect to the median line of the orthonormal reference frame in a plane of the Y axis. For example, in the case of a position shifted backwards at a time t, the position along the Y axis has, for that time t, a negative value indicating a posterior hyper-support. This position can be measured, for example, in millimeters. FIG. 3B shows the discrete values of the "position of the pressure center along the Y axis" parameter 121b obtained from the statokinesigram 110 shown in FIG. 2.

The Radius in Polar Coordinates

This distance corresponds to the distance of the pressure center from the average position of the pressure center according to the orthonormal reference plane (0,0). For example, if the pressure center is shifted by 4 millimeters from the average position of the pressure center along an axis of 60°, at a time t, the radius in polar coordinates has, for that time t, a value of 4 millimeters. Such a transformation, for the first time proposed by the inventors, allows to quantify the overall distance of the pressure center from a point of origin without limiting to the X and Y coordinates of the center of gravity.

Transformations Associated with the Stability 122 of the Pressure Center Radial Balance The radial balance is the maximum distance of the pressure center from its current value at a given time over a predefined period of time of t seconds. The time taken into account for calculating the radial balance can be between 0.05 and 10 seconds, preferably between 0.1 and 2 seconds. The radial balance is calculated for all sampling points of the displacement of the pressure center over the duration of the acquisition. It is thus a function of time and can be measured, for example, in millimeters.

Time Balance

The time balance is the time required for the pressure center to move more than r millimeters away from its current position at any given time. The distance r taken into account for calculating the time balance can be between 0.1 and 20 millimeters, preferably from 1 to 10 millimeters Time balance is calculated for all sampling points of the displacement of the pressure center over the duration of the acquisition. It is thus a function of time and can be measured, for example, in seconds.

Ballistic Interval

The ballistic interval is the time interval between two balance positions. A balance position corresponds to a strong value of time balance. Preferably, a balance position corresponds to a time when the time balance is greater than 60%, preferably greater than 80%, of the maximum observed in the statokinesigram. The ballistic interval is calculated over the duration of the acquisition and the number of values obtained may vary depending on the acquisitions. It is not a function of time and can be measured, for example, in seconds. FIG. 4 shows, as a function of time, all the values of the "time balance" parameter calculated based on the statokinesigram 110 shown in FIG. 2. The values of the "ballistic interval" parameter 122a are, for example, expressed in seconds and correspond to the times between the values between P1 and P3, and P4 and P6. For example, this parameter comprises the values corresponding to the time differences between: P3-P2; P3-P1; P6-P1; P6-P2; P6-P3; P6-P5; P5-P1; P4-P3.

Transformations Associated with the Dynamics 123 of the Pressure Center Velocity of the Displacement of the Pressure Center The velocity of the displacement of the pressure center is calculated for all sampling points of the displacement of the pressure center over the duration of the acquisition. This parameter is thus a function of time and can be measured, for example, in millimeters.

Acceleration of the Displacement of the Pressure Center

The acceleration of the displacement of the pressure center is calculated for all sampling points of the displacement of the pressure center over the duration of the acquisition. This parameter is thus a function of time and can be measured, for example, in millimeters per second squared.

Power

The power according to the invention corresponds to the value of the scalar product of the velocity and acceleration calculated for all sampling points. This parameter represents the energy expended by the individual to change the norm of the velocity of the pressure center.

Deviation

The deviation according to the invention corresponds to the norm of the vector product of the velocity and acceleration calculated for all sampling points. This parameter represents the energy expended by the individual to change the direction of the velocity of the pressure center (namely its displacement, its trajectory or its movement).

In the context of the study of a statokinesigram 110, the power and deviation are two parameters that can advantageously replace the length of the displacement of the pressure center, the variance of the velocity as a function of the Y axis (VFY) or the LFS (namely ratio of length to surface), providing information according to the prior art on the energy consumption expended by the subject to control his/her posture. In particular, the deviation proposed by the inventors allows to evaluate from a new angle the energy expenditure of the individual and is more relevant in the method according to the invention than the parameters proposed in the prior art (e.g. VFY, LFS).

The quantification method 1 according to the invention may also comprise a step of determining 30 several quantifiers 130 from the trajectory parameters 120. This determination step 30 can be performed by a data processing module 220. Once the trajectory parameters 120 are generated during the extraction step 20 of the trajectory data of the pressure center, the work of the prior art generally focused exclusively on the mean and the variance of these parameters over an acquisition period.

In the method developed by the inventors, the latter were interested in many other methods for transforming these parameters in order to generate, from these sets of values and in combination with other sets of values, a single value representative of the balance of an individual. Thus, new quantifiers never used in the past were generated.

The step of determining 30 several quantifiers 130 from the trajectory parameters 120 therefore consists in transforming, for each trajectory parameter 120, all the values into a single value that can be used in the context of a comparison, for example via a statistical comparison model. This transformation into a single value (quantifiers) can be repeated for several trajectory parameters or for a same trajectory parameter. FIG. 5 shows some of these quantifiers as calculated for the "position of the pressure center along the X axis" parameter.

The most informative quantifiers in the context of the quantification method according to the invention are the mean value, the median value, the variance, the square mean, or an extreme value, of an extracted trajectory parameter 120. Thus, preferably, the quantification method 1 according to the invention includes, for at least one parameter, calculating the mean value 127, the median value 128, the variance, the square mean or at least one extreme value, of said trajectory parameter (121, 122, 123). Even more preferably, the quantification method 1 according to the invention includes, for at least one parameter, calculating at least one extreme value of said parameter.

The extreme values of a parameter are obtained by determining a percentile. A percentile, or centile, can be calculated, for example, by ordering and then sorting all the values of a parameter in 100 subsets with a same number of values. FIG. 5 shows the 10 percentile 126 and the 95 percentile 129 of the "position of the pressure center along the X axis" parameter corresponding to the highest value of the position of the pressure center along the X axis within the lowest 10% of values and the lowest value of the position of the pressure center along the X axis within the highest 5% of values, respectively. Thus, the 10 percentile is the value separating 10% of the lowest values and 90% of the highest values while the 95 percentile is the value separating 95% of the lowest values and 5% of the highest values. Preferably, an extreme value of a trajectory parameter 120 corresponds to a percentile less than or equal to 15 or to a percentile greater than or equal to 85; more preferably, to a percentile less than or equal to 10 or to a percentile greater than or equal to 90 and even more preferably to a percentile less than or equal to 5 or to a percentile greater than or equal to 95.

Alternatively, an extreme value of a trajectory parameter 120 may correspond to a percentile greater than or equal to the 5 percentile and less than or equal to the 15 percentile (low extreme values) or to a percentile greater than or equal to the 85 percentile and a percentile less than or equal to the 95 percentile (high extreme values).

In addition, beyond the calculation of a quantifier 130, the inventors showed that the comparison eyes open (O)/eyes closed (F) on some parameters or quantifiers would allow to differentiate performance in terms of balance. Thus, in particular, the quantification method 1 according to the invention includes for at least one quantifier, calculating an O/F or F/O ratio.

During their developments, the inventors selected a set of quantifiers 130 that were particularly relevant for quantifying the balance. Preferably, in the context of the quantification method 1 according to the invention, the quantifier linked to the position of the pressure center is selected from the following values:
    the mean or median value on the X or Y axis of the pressure center,
    the mean value of the squares of the values on the X or Y axis of the pressure center,
    the extreme values on the X or Y axis of the pressure center, and
    the variance on the X or Y axis of the pressure center.

In particular, in the context of the quantification method 1 according to the invention, the quantifier linked to the extreme values on the X or Y axis of the pressure center is selected from:
    the low extreme values of the position of the pressure center along the transverse axis (Y), preferably within the percentiles less than or equal to 10, these values correspond to the maximum observed retropulsion, and
    the high extreme values of the trajectory of the pressure center along the transverse axis (Y), preferably within the percentiles greater than or equal to 90.

Preferably, the quantification method according to the invention includes calculating at least one, more preferably at least two, quantifiers linked to the position of the pressure center that can be independently selected from the following quantifiers:
    the 15 percentile, preferably the 10 percentile and even more preferably the 5 percentile of the position of the pressure center on the X axis, preferably for a displacement of the pressure center measured while the individual had his/her eyes closed,
    the median value on the Y axis of the pressure center, preferably for a displacement of the pressure center measured while the individual had his/her eyes closed,
    the median value on the X axis of the pressure center, preferably for a displacement of the pressure center measured while the individual had his/her eyes open,
    the 15 percentile, preferably the 10 percentile and even more preferably the 5 percentile of the position of the pressure center on the Y axis, preferably for a displacement of the pressure center measured while the individual had his/her eyes closed,
    the variance on the Y axis of the trajectory of the pressure center, preferably for a displacement of the pressure center measured while the individual had his/her eyes closed,
    the variance on the X axis of the trajectory of the pressure center, preferably for a displacement of the pressure center measured while the individual had his/her eyes closed,
    the mean or median values on the Y axis and more particularly the ratio between these values for a statokinesigram recorded when the individual had his/her eyes open and these values for a statokinesigram recorded when the individual had his/her eyes closed,
    the extreme values of the radius in polar coordinates such as:
        the 15 percentile, preferably the 10 percentile and even more preferably the 5 percentile of the radius in polar coordinates of the pressure center, preferably for a displacement of the pressure center measured while the individual had his/her eyes closed,
        the 85 percentile, preferably the 90 percentile and even more preferably the 95 percentile of the radius in polar coordinates of the pressure center, preferably for a displacement of the pressure center measured while the individual had his/her eyes open,
    the median of the radius in polar coordinates of the pressure center, and
    the mean value of the squares of the radius in polar coordinates of the pressure center.

Preferably, the quantification method 1 according to the invention includes calculating at least one, more preferably at least two, quantifiers linked to the stability of the pressure center that can be independently selected from the following quantifiers:

the 10 percentile of the radial balance for a duration of 0.5 seconds, preferably for a displacement of the pressure center measured while the individual had his/her eyes closed, the 90 percentile of the radial balance for a duration of 0.1 seconds, preferably for a displacement of the pressure center measured while the individual had his/her eyes open, the variance of the time balance for a distance between 1 and 10 millimeters, preferably from 1 to 5 millimeters, preferably the ratio of the value obtained for a displacement of the pressure center measured while the individual had his/her eyes open to the value obtained for a displacement of the pressure center measured while the individual had his/her eyes closed, the mean value, the square mean value or the median value, preferably the mean value of the ballistic interval values, preferably for a displacement of the pressure center measured while the individual had his/her eyes closed, and the extreme high values of the ballistic interval, that is to say between the 85 percentile and the 95 percentile, such as the 85 percentile, preferably the 90 percentile and even more preferably the 95 percentile of the ballistic interval.

Preferably, in the context of the quantification method according to the invention, the quantifier linked to the dynamics of the pressure center is selected from the mean, the median, the square mean or the variance of the power, preferably for a displacement of the pressure center measured while the individual had his/her eyes open.

Preferably, the quantification method according to the invention includes calculating at least one, more preferably at least two, quantifiers linked to the dynamics of the pressure center that can be independently selected from the following quantifiers:

the extreme low values of the acceleration of the displacement of the pressure center such as the 15 percentile, preferably the 10 percentile, the extreme low values of the deviation of the displacement of the pressure center, that is to say between the 5 percentile and the 15 percentile, such as the 15 percentile, preferably the 10 percentile, even more preferably the 5 percentile, preferably for a displacement of the pressure center measured while the individual had his/her eyes open, and the extreme high values of the velocity of displacement of the pressure center such as the 85 percentile, preferably the 90 percentile, preferably for a displacement of the pressure center measured while the individual had his/her eyes open.

For the first time, the inventors propose a multiparameter method based on the combination of a plurality of parameters and/or quantifiers. Thus, in addition to extracting at least one parameter linked to the stability 122 of the pressure center and at least one parameter linked to the position 121 of the pressure center, they determined that, in order to obtain a more reliable value in the quantification method 1 according to the invention, it is preferable to calculate and then combine several quantifiers, for example several quantifiers related to the same trajectory parameter. Thus, in order to quantify the balance in the best way possible and more particularly to predict a risk of falling, it is preferable to calculate, from the trajectory parameters 120, at least five quantifiers 130, even more preferably at least eight quantifiers 130.

The inventors also propose for the first time the combined use of a BMI category 150 with quantifiers linked to the trajectory of the pressure center. Thus, they determined that, in order to obtain a reliable value in the quantification method 1 according to the invention and in order to quantify the balance in the best way possible and more particularly to predict a risk of falling, in addition to combining several quantifiers, classifying the one or more statokinesigram(s) according to the BMI value is advantageous.

Thus, the quantification method 1 according to the invention includes a step of comparing 40 several values of quantifiers 130 with the values of the same quantifiers obtained from reference statokinesigrams 111, preferably classified in the same BMI category 150 as the BMI category 150 determined in step b).

The comparison step can be implemented using a data processing module 220 and can be performed using known statistical methods. Preferably, this comparison step 40 can be performed using comparison, classification or learning models such as: perceptron, Kernel, Multiple kernel learning, Support vector machine, decision trees, random forests, Bagging, AdaBoost, k-nearest neighbor and/or penalized linear Fisher discriminant.

Among the statistical methods, linear regression models are simple and easy to implement. However, these linear models are limited because of the linearity hypothesis and are not optimal for the quantification method 1 according to the invention. Thus, the comparison step 40 includes using a non-linear statistical model.

More preferably, the comparison step 40 is based on a model, trained on a dataset and configured to predict the label of a new observation of the population. For example, for calibration purposes, it is possible to use a dataset from a set of individuals representative of a population, characterized by several reference statokinesigrams 111 and their associated reference parameters and/or quantifiers and by a binary label (label or class), for example in the form of "good balance"/"poor balance". In the context of the present invention, the comparison is advantageous for reference statokinesigrams 111 classified in the same BMI category 150 as the BMI category of the statokinesigram 110 of the individual. Thus, the comparison step 40 may include a preliminary sub-step of categorizing the reference statokinesigrams 111 depending on the BMI data 16 attached to said reference statokinesigrams 111. The dataset can also comprise multiple labels. In the context of the present invention, the quantification method 1 may be based on at least twenty-five reference statokinesigrams 111, preferably at least fifty, and even more preferably at least one hundred.

The comparison step 40 includes using a supervised statistical learning model. Indeed, the inventors determined that, in the context of the quantification method 1 according to the invention, the best quantification results are obtained from methods based on supervised statistical learning principles, preferably methods adapted to multivariate data.

Within supervised learning methods, the inventors identified some more effective treatment methods. This could be linked to the fact that the quantifiers derived from the method according to the invention come from datasets having significant imbalance and generally non-uniform metrics. Thus, preferably, this comparison step 40 is performed using various non-linear supervised statistical learning methods. For example may be cited:

the kernel methods (e.g. Large Margin Separators—Support Vector Machines SVM, Kernel Ridge Regression) described, for example, in Burges, 1998 (Data Mining and Knowledge Discovery. A Tutorial on Support Vector Machines for Pattern Recognition).

the ensemble methods (e.g. Bagging, Boosting, decision trees, Random Forest) described, for example, in Brieman, 2001 (Machine Learning. Random Forests), or the neural networks described, for example, in Rosenblatt, 1958 (The perceptron: a probabilistic model for information storage and organization in the brain).

As discussed above, the purpose of the method according to the invention, beyond predicting which group of individual to belong to, is to quantify balance, that is to say to associate a numerical value or level of quality with the balance of an individual. Thus, the quantification method 1 according to the invention includes a step of determining 50 a value 160 representative of the balance of the individual based on the results of the comparison step 40.

Preferably, the representative value 160 can be based on the definition of an order relationship on the population in order to rank the individuals composing it. This step can be referred to as a binary ordering. In practice, the binary ordering problem consists in learning a model, from a sample $Sn=\{(Xi, Yi), 1 \le i \le n\}$ of a copy of the pair (X,Y) so as to order at least one new observation $X_0$ of the random variable X, for which the label $Y_0$ is not known. Such a model allows new observations to be ordered by placing at the top of the classification the observations with the highest probability of being positive and at the bottom of the classification with the observations most likely to be negative.

Alternatively, assigning this representative value 160 can be based on several statistical methods such as the flexible margin SVMs or the Gaussian Mixture Models.

Preferably, the balance quantification method 1 according to invention includes using a scoring algorithm 500 that can be integrated into a data processing module 220 and configured to implement:

the step of comparing 40 values of several quantifiers 130 with the values of the same quantifier obtained from reference statokinesigrams 111, advantageously classified in the same BMI category 150 as the BMI category of the statokinesigram 110 of the individual, and the step of determining 50 a value 160 representative of the balance of the individual at the end of the comparison.

This scoring algorithm 500 may have been built from different supervised learning models. Even more preferably, this scoring algorithm 500 is based on a supervised statistical learning model configured to minimize a risk of the ordering rule and thus allowing to obtain more efficient prediction rules such as the methods: Rankboost, Adarank, Rank SVM, Lambda rank, Ranking Forest or neural network. In addition, as part of the importance of the BMI categorization for quantifying the balance, the balance quantification method 1 according to the invention may include using a scoring algorithm 500 per BMI category 150.

Even more preferably, this or these scoring algorithms 500 may have been built from a combination of several non-linear supervised statistical learning models. Thus, preferably, creating the scoring algorithm 500 included a "Bagging" step and/or a Boosting step. For example, the scoring algorithm 500 may include several Ranking Tree type trees built using a Bagging step. Indeed, the scoring algorithms developed by the inventors in the context of the present invention are very effective if they include a Bagging step.

Even more preferably, the previously calibrated scoring algorithm 500 was obtained by implementing a Ranking Forest or Random Forest method.

Bagging, or Bootstrap Aggregating, is a method of training a learning algorithm on different subsets of the initial learning set. In practice, B subsets are generated by drawing each of them randomly N times and returning them to the initial learning set. The subsets are called bootstrap samples. Bagging and its implementation are described in detail in Galar et al 2011 (A Review on Ensembles for the Class Imbalance Problem: Bagging-, Boosting-, and Hybrid-Based Approaches). Bagging is very effective in combination with learning algorithms such as decision trees and the inventors also discovered that the underbagging method is particularly well suited to the method according to the invention.

Boosting encompasses a set of algorithms such as: Adaboost, LPBoost, TotalBoost, BrownBoost, xgboost, MadaBoost, LogitBoost. Boosting refers to a method of training a learning algorithm to produce accurate decisions by combining "weak" decision rules (namely able to recognize at least two classes as well as chance would do). Boosting allows, by successive iterations of weak rules, a strong classification rule, or decision rule, to be generated. Boosting is therefore a sequential method and each sample is drawn according to the performance of the basic rule on the previous sample. Boosting and its implementation are described in detail in Freund & Schapire 1999 (Machine Learning Large. Margin Classification Using the Perceptron Algorithm).

Random Forest analysis or Random Forest is one of the supervised statistical learning methods. It is based on the Bagging principle, the originality of the analysis is the aggregation of K trees built with a small number of variables. Each node is built with a small number of variables, but always constant and randomly selected. For example, several independent models are built to predict the same variable Y and then the predictions of these models are aggregated. This aggregation of independent models allows to reduce the variance and thus to reduce the prediction error.

Preferably, the quantification method 1 according to the invention allows to obtain a balance quantification in the form of a score or a value between zero and one hundred, proportional to the quality of the balance. For example, a value of less than 30 indicates a poor balance.

Preferably, the step of determining a balance value based on the results of the comparison is followed by a step of recording 60 the balance representative value 160 obtained and possibly associating said value with a unique identifier linked to said individual.

Thus, this allows the individual to compare his/her representative balance value 160 over time. Thus, preferably, the quantification method 1 according to the invention can be implemented in the same individual at different dates in order to track the evolution of his/her balance representative value 160 and therefore of the quality of his/her balance.

As shown in FIG. 1, the balance quantification method 1 according to the invention may also comprise a step of graphically representing 70 said balance representative value 160. The value can be subject to a display via a display module 340a. This display can be a simple display indicating a value or a graphical representation.

This graphical representation can show the evolution of the balance representative value 160 over time or the placement of this value within a group of individuals.

Said balance representative value 160 can also be transmitted to remote systems such as tablets, servers or personal computers. Thus, the quantification method 1 according to the invention may comprise a step of transmitting the balance representative value 160, the calculated quantifiers and/or the calculated parameters to at least one communicating system such as a tablet, a server or a computer, via at least one communication network.

Preferably, the invention relates to a balance quantification method 1 comprising quantifying the static balance and the dynamic balance. Even more preferably, the invention relates to the quantification of the static balance.

As part of the development of this new balance quantification method 1, the inventors verified the relevance of the balance representative value 160 obtained via the statistical models developed and especially the scoring algorithms used via ROC curves. The statistical models developed and especially the scoring algorithms 500 used by the inventors allow to obtain AUCs greater than 0.7, preferably greater than 0.8.

FIG. 6 shows a particular embodiment of the invention. From this embodiment, the inventors analyzed the statokinesigrams of 49 individuals as shown in the examples. FIG. 10 shows a particular embodiment of the invention. From this embodiment, the inventors analyzed the statokinesigrams of 84 individuals as shown in the examples.

FIGS. 7A and 7B show two decision trees according to the invention as built by a Ranking Forest model. FIG. 7b shows a decision tree preceded by a step 15 of classifying the statokinesigram 110 in a BMI category 150 (e.g. BMI<21) depending on the BMI value 16 of the individual, represented here as a binary choice.

F1 and F2 correspond, within the meaning of the invention, to quantifiers related to a parameter linked to the position 121 of the pressure center. In addition, the 90 percentile of the ballistic interval is a particularly preferred quantifier within the meaning of the invention.

F3 corresponds to a quantifier related to the stability 122 of the pressure center.

The combination of these quantifiers via a scoring algorithm 500 allows to generate a balance representative value 160 (e.g. 0; 0.33; 0.66; 1).

According to one aspect, the invention relates to a balance quantification device 2 able to implement the balance quantification method 1 according to the invention.

More particularly, the balance quantification device 2 according to the invention includes:
 a communication module 210, able to receive a statokinesigram 110 of said individual, for example able to receive data comprising at least one statokinesigram of said individual,
 a storage means 280, and
 a data processing module 220.

Alternatively, the balance quantification device 2 according to the invention includes:
 a communication module 210, able to receive data comprising at least one statokinesigram 110 of said individual and body mass index data 16 of said individual,
 a storage means 280, able to record the statokinesigram 110 and the BMI data 16,
 a classification module 250, and
 a data processing module 220.

A balance quantification device 2 according to the invention is shown schematically in FIG. 8. These modules are separate in FIG. 8, but the invention may provide for different types of arrangements, such as a single module combining all the functions described here. These modules can be divided into several electronic boards or gathered on a single electronic board.

The communication module 210 is configured to receive and transmit information to remote systems such as platforms, tablets, telephones, computers, or servers. The communication module allows to transmit the data on at least one communication network and may comprise a wired or wireless communication. Preferably, the communication is operated via a wireless protocol such as wifi, 3G, 4G, and/or Bluetooth.

The communication module 210 allows, for example, to receive the raw data of the displacement of the pressure center, the BMI data 16 or statokinesigrams 110. It is also configured to send data related to the calculated parameters, the calculated quantifiers and the balance representative value 160. These data exchanges may take the form of sending and receiving files containing the raw values of the pressure sensors, files containing the coordinates of the trajectory of the pressure center, and files including the parameters 120, the quantifiers 130, category data 150, body mass index data 16 of said individual and the balance representative values 160 determined from the statokinesigram 110.

The exchanged data can preferably be transferred in an encrypted form and associated with a key specific to the individual being studied.

The data processing module 220 is configured to:
 Extract, from a statokinesigram 110 of an individual transmitted by the communication module 210, values of at least one trajectory parameter related to the position 121 of the pressure center and values of at least one trajectory parameter related to the stability 122 of the pressure center,
 Determine several quantifiers 130, from the values of the extracted trajectory parameters 121, 122,
 Compare the values of said quantifiers 130 with the values of the same quantifiers obtained from reference statokinesigrams 111, and
 Determine a value 160 representative of the balance of the individual based on said comparison.

Alternatively, the data processing module 220 is configured to:
 Extract, from a statokinesigram 110 of an individual transmitted by the communication module 210, values of at least one trajectory parameter related to the position 121 of the pressure center, to the stability 122 of the pressure center and/or to the dynamics 123 of the pressure center,
 Determine several quantifiers 130, from the values of the extracted trajectory parameters 121, 122, 123,
 Compare the values of said quantifiers 130 with the values of the same quantifiers obtained from reference statokinesigrams 111 classified in the same BMI category 150 as the BMI category of the statokinesigram 110 of the individual, and
 Determine a value 160 representative of the balance of the individual based on said comparison.

Advantageously, the data processing module 220 has a processor and is able to connect to a storage means 280.

The storage means 280 may comprise a transient memory and/or a non-transient memory. It is able to record, for example in the form of files, the raw values of the pressure sensors, the coordinates of the trajectory of the pressure center, the parameters 120, the quantifiers 130, the BMI data 16, the BMI category data 150 and the balance representative values 160 determined from the one or more statokinesigram(s) 110. The non-transient memory allows, for example, the configuration of the data processing module to be recorded, while the non-transient memory allows, for example, the statokinesigram 110 to be recorded. The non-transient memory can be a medium such as a CD-rom, a memory card, or a hard drive hosted on a remote server.

Preferably, the data processing module 220 is configured to implement the different steps of the quantification method 1 according to the invention. Thus, the preferred steps of the balance quantification method 1 according to the invention are also preferred configurations for the data processing module 220 according to the invention.

The quantification device 2 according to the invention may also include a module 230 for generating a statokinesigram 110. This module is configured to generate the data related to a statokinesigram 110 (e.g. position along the x- and y-axes as a function of time) from raw data of the displacement of the pressure center such as generated by force or pressure sensors.

The quantification device 2 according to the invention may also include a re-sampling module 240. Indeed, not all devices able to generate raw data of the displacement of the pressure center or statokinesigrams 110 provide a controlled sampling frequency. Thus, some devices may lead to a statokinesigram 110 being generated with a first random frequency, the frequency of which cannot be predicted because it constantly varies during the acquisition, for example, for a same statokinesigram 110, between 10 and 1000 Hz. However, such a frequency variation can lead to decreases in the performance of the balance quantification method 1 according to the invention. Thus, preferably, the re-sampling module is configured to process the raw data or the statokinesigrams 110 at a first frequency in order to generate statokinesigrams 110 re-sampled at a second frequency and with a substantially constant frequency. By substantially constant frequency, is to be understood a frequency varying by less than 10% within the statokinesigram 110, preferably varying by less than 5%, and even more preferably by less than 1%.

The statokinesigram 110 at a second frequency, generated by the re-sampling module 240, has a sampling frequency equal to at least 25 Hz. Preferably, the second frequency is substantially identical to the frequency of the reference statokinesigrams 111.

The balance quantification method according to the invention comprises a classification module 250 configured to classify a statokinesigram 110 of the individual in a body mass index (BMI) category 150 depending on the BMI 16 of said individual.

The balance quantification device according to the invention may comprise a denoising module 290 configured to filter the raw data generated by the pressure or force sensors in order to reduce or suppress interference signals. Denoising can be based on various methods such as wavelet denoising, thresholding, Wiener filter and deconvolution.

The device may also comprise a control interface 260. This control interface is configured to allow a user to interact with the balance quantification device. It may comprise, for example, manual actuators (e.g. buttons) or a touch screen able to receive user commands.

The device may also comprise a display module 270. This display module may comprise a liquid crystal display. It allows to display various information such as the results of the quantification, the balance representative value 160, the progression over time of said value and its positioning in relation to the balance representative values 160 within a group of persons.

According to another aspect, the invention relates to a balance quantification system 3 shown in FIG. 9, adapted to implement the quantification method 1 according to the invention. Preferably, the system 3 for quantifying the balance of an individual comprises:
  a platform 310, said platform 310 being adapted to receive an individual and comprising pressure and/or force sensors 312 configured to generate raw data 313, at a first frequency, as a function of a pressure exerted by the feet of the individual on the platform 310,
  a raw data processing unit 320, arranged to obtain at least one statokinesigram 110 of the individual from the raw data 313 generated by the platform 310, and
  a described previously balance quantification device 2, able to communicate with the processing unit 320.

As shown in FIG. 9, the platform 310 according to the invention is a support intended to receive an individual and able to measure the displacement of a pressure center using force and/or pressure sensors. Any sensor system for measuring the pressure center can be used. The only requirement is that the platform 310 must be able to produce raw data for positioning the pressure center. This support can, for example, be a pair of soles, an "intelligent" floor equipped with sensor or a scale. Preferably, the platform 310 has a tray 311. As a general rule, the dimensions on one side of the tray 311 may be between 15 and 70 cm, preferably in the order of 25 to 40 cm. This tray 311 can, for example, include a template allowing for a reproducible positioning of the feet, between individuals and over time for a same individual.

The platform 310 is configured to measure the pressure or forces applied onto the tray at a given time and includes sensors 312 to that end. The sensors will transform the applied force into an electrical, optical or magnetic signal corresponding to the raw data. These raw data can be combined and processed so as to specify the coordinates of the pressure center and to track its variations over time. These sensors can be pressure or force sensors. A force sensor measures the resultant of the support forces of a standing subject. The measurement of the forces and moments exerted at the platform allows to specify the coordinates of the pressure center and to track its variations over time. A pressure sensor may comprise, for example, a pressure cell configured to measure or detect the pressure induced by the weight of the individual placed on the tray or the pressure exerted by the feet of the individual on the platform. The data derived from these sensors are the raw data. The platform 310 can also comprise a plurality of resistive or piezo electric sensors (for example between 1,000 and 6,000 sensors). There are preferably 4 sensors, located at the ends of the platform, for example 20 to 50 cm apart for the right and left or top and bottom sensors. For example, as shown in FIG. 9, the platform 310 has four sensors 312 located at the four corners of the tray (Top left, Top right, Bottom left, Bottom right).

The platform 310 advantageously includes a time counting module and can be configured to measure the values of its various sensors 312 at a random interval, at a frequency that can vary, for example, from 10 Hz to 1,000 Hz. Preferably, the platform 310 is configured to measure the values of its various sensors 312 at a frequency greater than or equal to 25 Hz, more preferably greater than or equal to 50 Hz.

Even more preferably, the platform 310 is configured to measure, when acquiring a statokinesigram 110, the values of its various sensors 312 at a frequency greater than or equal to 25 Hz and in a substantially constant manner. Indeed, if the sampling frequency is too low, or too random, the quantification of the balance will not be sufficiently accurate. If the frequency is not constant then preferably the average acquisition frequency is greater than or equal to 60 Hz, more preferably greater than or equal to 75 Hz.

The platform 310 may include a display device, preferably positioned so that the individual standing on the tray 311 can see the display device.

The platform 310 may also include a speaker device that can give instructions to the individual (e.g., get on or off the tray 311). These instructions can also be given by the display device.

The platform 310 can also include a module for measuring the weight of the individual, his/her fat, water, bone, muscle mass, his/her heart rate and/or his/her body mass index.

The balance quantification system 3 also includes a unit for processing the raw data 320 generated by the platform. This raw data processing unit 320 is arranged and/or configured to generate at least one statokinesigram 110 of the individual from the raw data generated by the sensors 312. This raw data processing unit 320 can be integrated, for example, into the platform 310 as shown in FIG. 9. However, it can also be integrated into a remote server 330, into the quantification device 2 (e.g. it then also integrates the module 230 for generating a statokinesigram 110) or into a control device 340.

The balance quantification system 3 may include a remote server 330 as shown in FIG. 9. For example, it is possible to access this remote server 330 via a web interface or directly via the appropriate functions directly implemented on a control device 340. All communications between the one or more control device(s) 340 and the remote server 330 can be secured, for example, by HTTPS protocols and AES 512 encryption.

This remote server can host the quantification device 2. Thus, a single quantification device 2 can track a plurality of individuals.

The quantification system according to the invention may include a system control device 340 configured to interact with the platform 310 and the balance quantification device 2. This system control device 340 allows, for example, to control the data acquisition from the platform 310 and to display the results from the quantification device 2.

This system control device 340 is preferably a mobile device such as a tablet 340*a*, a laptop, or a watch.

The quantification system according to the invention may include a BMI determination device 350 configured to determine, from height and weight data, the BMI of an individual.

According to another aspect, the invention relates to a computer program product 4 configured to implement the balance quantification method 1 according to the invention. The computer program product 4 is recorded on a non-transient memory medium and is able to run on a computer, a tablet or a server; said computer program including at least:
- an algorithm adapted to extract, from a statokinesigram 110 of an individual, values of at least one trajectory parameter related to the position 121 of the pressure center and values of at least one trajectory parameter related to the stability 122 of the pressure center
- an algorithm adapted to determine several quantifiers 130, from the values of the extracted trajectory parameters 121, 122,
- an algorithm adapted to compare the values of said quantifiers 130 with the values of the same quantifiers obtained from reference statokinesigrams 111, and
- an algorithm adapted to determine a value 160 representative of the balance of the individual based on said comparison.

Alternatively, the invention relates to a computer program product 4 configured to implement the balance quantification method 1 according to the invention. The computer program product 4 is recorded on a non-transient memory medium and is able to run on a computer, a tablet or a server; said computer program including at least:
- an algorithm adapted to classify a statokinesigram 110 of an individual in a body mass index (BMI) category 150 depending on the BMI 16 of said individual,
- an algorithm adapted to extract, from a statokinesigram 110 of an individual, values of at least one trajectory parameter related to the position 121 of the pressure center, to the stability 122 of the pressure center and/or to the dynamics 123 of the pressure center,
- an algorithm adapted to determine several quantifiers 130, from the values of the one or more extracted trajectory parameters 121, 122, 123,
- an algorithm adapted to compare the values of said quantifiers 130 with the values of the same quantifiers obtained from reference statokinesigrams 111 classified in the same BMI category 150 as the BMI category 150 of statokinesigram 110, and
- an algorithm adapted to determine a value 160 representative of the balance of the individual based on said comparison.

More preferably, the computer program product 4 is recorded on a non-transient memory medium and is able to run on a computer, a tablet or a server; said computer program including at least:
- optionally, an algorithm adapted to classify a statokinesigram 110 of an individual in a body mass index (BMI) category 150 depending on the BMI 16 of said individual,
- an algorithm adapted to extract, from a statokinesigram 110 of an individual, values of at least one trajectory parameter related to the position 121 of the pressure center, values of at least one trajectory parameter related to the stability 122 of the pressure center and values of at least one trajectory parameter related to the dynamics 123 of the pressure center,
- an algorithm adapted to determine several quantifiers 130, from the values of the extracted trajectory parameters 121, 122, 123, and
- a scoring algorithm adapted to compare the values of several quantifiers 130 and determine a value 160 representative of the balance of the individual based on said comparison.

The method, device, system and computer program product according to the invention allow for the quantification of the balance of an individual and can have many applications.

Indeed, the invention allows to provide a measurement tool, namely a method, the device for implementing the method and the system integrating the device, for obtaining a numerical and objective value of the balance of an individual in order to answer three main questions related to the balance of an individual:
A] the evolution of the balance, natural or under treatment,
B] the quality of the balance and therefore, its corollary, the severity of a possible balance disorder (e.g. what is the risk of falling?), and
C] the one or more causes of the possible balance disorder.

Indeed, generating a value 160 representative of the balance of an individual and indicative of the quality of his/her balance allows the individual, or others, to assign a numerical and objective value to this balance.

These values or scores can be used as part of a monitoring over time to identify deviations from the learned reference.

Similarly, the invention can be used to highlight the effects of different treatments and the recovery rate could be tracked by the quantification of the balance according to the invention. Thus, the invention can be implemented in the context of performance evaluation of sports programs, prostheses, sports shoes, compensation insoles, rehabilitation protocols, neurological disorder treatment and/or surgical techniques. The method according to the invention is particularly adapted to the elderly.

In addition, the invention can be used to compare the quality of the balance of an individual with the quality of the balance of other individuals and determine, for example, whether the individual is at risk of falling. Thus, the invention can be implemented as part of the measurement of a risk of falling, for example, at 6 months. In this context, the balance representative value 160 determined by the quantification method 1 according to the invention, is an indicative value of a risk of falling at 6 months. In particular, the individual, within the meaning of the invention, is a person over 60, preferably over 70.

In addition, comparing the values of the quantifiers 130 obtained in an individual with values of the quantifiers obtained in different categories of people can help to target how the individuals should be cared for and to direct them to appropriate services (e.g. traumatology, rheumatology, neurology). Thus, the invention can be implemented in the context of determining the origin of the balance disorder.

EXAMPLES

Individuals Studied

The results shown below were achieved according to a protocol approved by the "Agence National de Sécurité du Medicament et des produits de santé" and written consent was obtained for all participants.

The invention was implemented on a first group of 49 individuals with the following characteristics:
over the age of 70;
able to stand on the platform,
BMI of less than 21 at the time of the consultation, and has given informed consent.

Among the 49 individuals included in the study:
27 reported a fall within the 6 months prior to the consultation,
7 falls led to trauma and hospitalization,
16 led to trauma and no hospitalization, and
4 were classified as benign (no trauma, no hospitalization).

The invention was also implemented on a second group of 84 individuals. Participants were recruited from different sites, the neurology department of the Val-de-Grace Hospital (Paris, France), the emergency department of the Begin Hospital (Paris, France) and the consulting room of a practitioner (Paris, France). The inclusion criteria were similar to the $1^{st}$ group of individuals: over the age of 65; referred to a general medical or neurological consultation, able to stand on the platform, not suffering from a balance-related disability, gave informed consent.

Only healthy individuals, that is to say asymptomatic individuals after clinical examination, were included in this study. Subjects with significant hypertension (mean systolic blood pressure (SBP) 140 mmHg or mean diastolic blood pressure (DBP) 90 mmHg), hypotension (SBP 90 mmHg or DBP 60 mmHg), with particular alterations or taking medication that could significantly alter their balance (such as vasoactive, psychotropic drugs) were excluded.

Measurement of the Displacement of the Pressure Center

During the consultation, the movements of the pressure center of the individuals were tracked using a Wii Balance Board (registered trademark) and recorded using a custom application specially developed as part of the invention. The feet were positioned in the most comfortable position for the patient, without exceeding the width of the shoulders. The trajectory of the pressure center was recorded for 20 seconds with the eyes open, and then for 20 seconds with the eyes closed. The trajectory of the pressure center was recorded for 25 seconds with the eyes open, and then for 25 seconds with the eyes closed for the $2^{nd}$ group of individuals. A fall questionnaire was completed for each individual in order to record reported falls that occurred in the last 6 months.

Pre-Processing

Before calculating the statokinesigrams, the output of the raw signals by the WBB was denoised and re-sampled.

Statistical Analysis.

For each statokinesigram, fifteen quantifiers were calculated from the statokinesigrams.

The quantifiers obtained from the statokinesigrams of the references allow to set up a scoring algorithm based on a Ranking Forest algorithm such as the subpart of a decision tree shown in FIG. 7. F1 corresponds to the ratio eyes closed/eyes open for the 90 percentile of the ballistic interval, F2 is the ratio eyes closed/eyes open for the variance of the position on the Y axis and F3 is the variance of the time balance with the eyes closed. The quantifiers obtained from a statokinesigram to be analyzed serve as the input for this scoring algorithm which calculates a value, between 0 and 1, indicative of the balance and more particularly of the risk of falling of the individual. A low score corresponds to a high risk of falling, while a high score is characteristic of a low risk of falling. For each statokinesigram, five different parameters were calculated as follows:

1) the position of the CoP along the medial-lateral axis,
2) the position of the CoP along the anterior-posterior axis,
3) the distance between the position of the CoP and the center of the trajectory, or radius,
4) the instantaneous acceleration of the CoP and
5) the ballistic intervals, that is to say the distance between the density peaks, where the sway density is defined as the time small spatial circle centered around the current position.

Then these five indices are derived from these signals (the resulting quantifiers are defined below in Table 1). They encode a five-dimensional representation of the signal.

TABLE 1

Summary of the quantifiers used.

| Quantifier | Parameter category | Description |
|---|---|---|
| 1 | Position of the CoP | Median of the statokinesigram radius, during the recording with the eyes closed (cm). |
| 2 | Stability of the CoP | Variance of the ballistic intervals of the signal, during the recording with the eyes open. (s2) |

TABLE 1-continued

Summary of the quantifiers used.

| Quantifier | Parameter category | Description |
|---|---|---|
| 3 | Dynamics of the CoP | 10th percentile of the norm of the acceleration, during the recording with the eyes closed (cm · s−2). |
| 4 | Position of the CoP | Variance of the values of the anterior-posterior coordinate of the signal, with the eyes closed (cm2) |
| 5 | Position of the CoP | Ratio (eyes closed/eyes open values) of the 10th of the values of the medial lateral coordinate of the signal. (No unit) |

Thus, unlike the prior art, the invention provides a measuring tool for obtaining a numerical and objective value for the balance of an individual.

Results of the 2$^{nd}$ Group of Individuals.

The basic data on age, gender, weight, height of the participants were collected and are shown in the table below (Table 2).

TABLE 2

Demographic data of the patients included in the sample. Fallers are patients who reported at least one fall in the previous 6 months. No significant differences were found in the 2 populations with respect to gender, age, weight, height and body mass index (BMI).

|  | Total | Non-fallers | Fallers |
|---|---|---|---|
| Demographic data | 84 | 60 | 24 |
| Male | 40 | 27 | 13 |
| Female | 44 | 33 | 11 |
| Age | 80.3 (±6.4) | 79.8 (±6.6) | 81.3 (±5.8) |
| Weight (kg) | 70.0 (±10.5) | 70.1 (±10.5) | 68.5 (±10.5) |
| Size (cm) | 167.1 (±8.4) | 167.2 (±8.4) | 167.0 (±8.4) |
| BMI (kg · m$^{−2}$) | 24.90 (±2.39) | 24.95 (±2.4) | 24.78 (±2.3) |

In our population, most of the quantifiers used individually, except for the quantifier (5), did not show significant results by the conventional Wilcoxon test (p<0.05), and their performance in ROC analysis was close to that of a random classifier (AUC between 0.49 and 0.54), questioning the ability of a single descriptor to properly classify the two groups and quantify the balance (Table 3).

TABLE 3

Mean and standard deviation for fallers and non-fallers, AUC, p-value for the test of the sum of Wilcoxon ranks for each of the quantifiers used.

| Quantifiers | Average for fallers | Average for non-fallers | AUC | p(Wilcoxon) |
|---|---|---|---|---|
| 1 | 0.69 (±0.40) | 0.53 (±0.21) | 0.49 | 0.37 |
| 2 | 71.48 (±23.20) | 95.21 (±102.19) | 0.53 | 0.62 |
| 3 | 0.011 (±0.009) | 0.007 (±0.004) | 0.54 | 0.18 |
| 4 | 0.77 (±0.64) | 0.42 (±0.29) | 0.52 | 0.09 |
| 5 | −0.42 (±2.77) | 0.78 (±1.87) | 0.53 | 0.008 |
| Invention | — | — | 0.75 | — |

In Table 3, the inventors observed that the indices alone cannot classify the fallers non-fallers. This could be due to the fact that, in our population, some fallers and non-fallers have very similar statokinesigrams. For example, some subjects prone to falling have larger statokinesigrams and a high variance of the anterior-posterior coordinates, while others may have a narrow CoP trajectory.

In Table 3, the inventors observed that these inherently contradictory properties question the classification accuracy of linear approaches, since the methods tend to mislabel one or more categories of fallers.

In addition, although the use of the quantifier (1) alone produces a near-random AUC, it showed a significant p-value in the Wilcoxon test (see Table 3). Conversely, the Ranking Forest approach, which combines all quantifiers in a complex and non-linear way, allows to obtain a significant AUC of 0.75. The ROC curve obtained by these methods is shown in FIG. 10.

Finally, Table 4 shows the quantifier importance relative mean used in this example. It should be noted that all quantifiers were considered important by the algorithm, which may highlight the need to use several different quantifiers when analyzing statokinesigrams.

TABLE 4

Mean and standard deviation of the importance of the quantifiers (Quant. Imp.) used in this example.

| Quantifier | 1 | 2 | 3 | 4 | 5 |
|---|---|---|---|---|---|
| Quant. Imp. | 0.20(±0.02) | 0.16(±0.02) | 0.20(±0.02) | 0.20(±0.02) | 0.25(±0.02) |

CONCLUSION

In this study, a new approach was proposed to classify fallers and non-fallers in an elderly population (84 individuals). This approach, based on the Ranking Forest type algorithm, combines the advantages of having robust classification performance while using only two simple static measurements. In this model, statokinesigrams are characterized in a multidimensional space (five quantifiers) and evaluated with a non-linear scoring algorithm that was formed using a subset of 70% of the global data set (learning set). This performance was validated in the remaining 30%.

The results were compared with the performance of each entity, showing that although each feature almost has a random performance in the classification of fallers, non-fallers, the Ranking Forest score achieves significantly higher performance.

In conclusion, the method according to the present invention allows to obtain significant information on the prediction of the risk of future falls, and can be extracted even via simple one-minute protocols.

The invention claimed is:

1. A method for quantifying the balance of an individual to obtain a value representative of the balance of said individual, said method being implemented by a device comprising at least one processor connected to a memory and said method comprising:
   a) a step of recording, on the memory, at least one statokinesigram of the individual obtained from a platform comprising pressure and/or force sensors,
   b) a step of extracting, by the processor and from the at least one statokinesigram of the individual recorded on the memory, values of at least one position trajectory parameter of a pressure center and values of at least one stability trajectory parameter of the pressure center, wherein the at least one position trajectory parameter of the pressure center is selected from: the position of the pressure center along an X axis, the position of the pressure center along a Y axis, and a radius in polar coordinates, wherein the at least one stability trajectory parameter of the pressure center is selected from: a radial balance, a time balance, and a ballistic interval,
   c) a step of determining, by the processor, values of a plurality of quantifiers, from the values of the trajectory parameters extracted in step b), at least one of the plurality of quantifiers determined in step c) being selected from: a mean value, a median value, a variance value, a mean square value, and an extreme value, of at least one of said trajectory parameters,
   d) a step of comparing, by the processor, said values of the plurality of quantifiers with values of the same quantifiers obtained from reference statokinesigrams, wherein the comparing is based on applying a learning model that is trained on a dataset from a set of individuals representative of a population and characterized by the reference statokinesigrams and the same quantifiers, the learning model configured to generate a prediction of an observation that is associated with the dataset, the learning model comprising a non-linear statistical model, and
   e) a step of determining, by the processor, said value representative of the balance of the individual at the end of the comparison.

2. The method according to claim 1, wherein:
   the recording step further comprises recording body mass index (BMI) data of said individual, and is followed by a step of classifying, by the processor, the at least one statokinesigram of the individual in a BMI category depending on the recorded BMI data, said classification step taking place after the recording step a) and before the extraction step b),
   during the step of comparing said values of said plurality of quantifiers, said values of said plurality of quantifiers are compared with the values of the same quantifiers obtained from reference statokinesigrams classified in the same BMI category as the BMI category determined during the classification step.

3. The method according to claim 2, wherein the BMI category determined in the classification step is selected from at least three BMI categories.

4. The method according to claim 1, wherein step b) further comprises extracting values of at least one dynamics trajectory parameter of the pressure center.

5. The method according to claim 4, wherein the at least one dynamics trajectory parameter of the pressure center is selected from: a velocity of displacement of the pressure center, acceleration of the displacement of the pressure center, a power and the deviation.

6. The method according to claim 1, wherein the at least one position trajectory parameter of the pressure center comprises its radius in polar coordinates.

7. The method according to claim 1, wherein step b) is performed from two statokinesigrams generated during a Romberg test.

8. The method according to claim 1, wherein at least one of the quantifiers determined in step c) is an extreme value of one of said trajectory parameters, said extreme value corresponding to a percentile greater than or equal to 5 and less than or equal to 15, or to a percentile greater than or equal to 85 and less than or equal to 95, of the trajectory parameter values.

9. The method according to claim 2, wherein steps d) and e) are performed by implementing the values of the quantifiers determined in step c) in a scoring algorithm previously calibrated based on the values of the same quantifiers obtained from the reference statokinesigrams.

10. The method according to claim 9, wherein the scoring algorithm is previously calibrated based on the values of the same quantifiers obtained from the reference statokinesigrams classified in the same BMI category as the BMI category determined in step a).

11. The method according to claim 10, wherein the previously calibrated scoring algorithm is obtained by implementing a supervised learning statistical method comprising implementing a Bagging step.

12. The method according to claim 1, further comprising, in step c), determining the values of at least five quantifiers.

13. The method according to claim 1, wherein:
   in step b), the extraction step is performed from a first said statokinesigram obtained while the individual's eyes are open and a second said statokinesigram obtained while the individual's eyes are closed; and
   in step d), the comparing step comprises comparing values of the same quantifiers obtained from the first and second said statokinesigrams obtained with the eyes closed or with the eyes open.

14. The method according to claim 1, further comprising determining, by the processor, a risk of the individual falling within a predetermined period of time based on the value representative of the balance of the individual.

15. The method according to claim 1, further comprising ranking, by the processor, the individual within a binary label classification based on the value representative of the balance of the individual.

16. The method according to claim 1, further comprising tracking, by the processor, progression of the value representative of the balance of the individual by one or more of: monitoring an evolution of the value over a predetermined period of time; monitoring a position of the value relative to other individuals; or identifying deviations of the value relative to a reference value.

17. The method according to claim 1, further comprising evaluating, by the processor, the value representative of the balance of the individual to at least one or more of: target customized treatment for the individual; or determine an origin of a balance disorder associated with the individual.

18. The method according to claim 1, wherein the learning model is configured to generate the prediction of the observation based on a binary label classification.

19. The method according to claim 1, wherein steps (d) and (e) are performed by implementing the values of the plurality of quantifiers in a scoring algorithm previously calibrated based on the values of the same quantifiers obtained from the reference statokinesigrams, the previously calibrated scoring algorithm having been obtained by implementing a supervised statistical learning model that is built from a combination of a plurality of non-linear supervised statistical learning models that are configured to aggregate predictions of a same, randomly selected variable.

20. A device for quantifying the balance of an individual, said device comprising:
- a receiver and/or transmitter configured to receive at least one statokinesigram of said individual,
- a memory configured to record the at least one statokinesigram, and
- at least one processor configured to connect to the memory and configured to:
  - Extract, from the at least one statokinesigram of said individual transmitted by the receiver and/or transmitter, values of at least one position trajectory parameter of a pressure center and values of at least one stability trajectory parameter of the pressure center, wherein the at least one position trajectory parameter of the pressure center is selected from: the position of the pressure center along an X axis, the position of the pressure center along a Y axis, and a radius in polar coordinates, wherein the at least one stability trajectory parameter of the pressure center is selected from: a radial balance, a time balance, and a ballistic interval,
  - Determine a plurality of quantifiers from the values of the extracted trajectory parameters, at least one of the plurality of quantifiers being selected from: a mean value, a median value, a variance value, a mean square value, and an extreme value, of at least one of said trajectory parameters,
  - Compare values of said plurality of quantifiers with values of same quantifiers obtained from reference statokinesigrams, wherein the comparison is based on applying a learning model that is trained on a dataset from a set of individuals representative of a population and characterized by the reference statokinesigrams and the same quantifiers, the learning model configured to generate a prediction of an observation that is associated with the dataset, the learning model comprising a non-linear statistical model, and
  - Determine a value representative of the balance of the individual based on said comparison.

21. The device according to claim 20, wherein:
the receiver/and or transmitter is further configured to receive BMI data from said individual,
the memory is further configured to record the BMI data,
the processor is further configured to classify the at least one statokinesigram of the individual in a BMI category depending on the BMI data of said individual, and
the processor is further configured to compare the values of said plurality of quantifiers with the values of the same quantifiers obtained from the reference statokinesigrams classified in the same BMI category as the BMI category of the at least one statokinesigram of the individual.

22. A system for quantifying the balance of an individual, comprising:
- a platform, said platform being configured to receive the individual and comprising pressure and/or force sensors configured to generate raw data, at a first frequency, as a function of a pressure exerted by feet of the individual on the platform,
- a processor configured to obtain at least one statokinesigram of the individual from the raw data generated by the platform, and
- the device according to claim 20, configured to communicate with the processor.

23. The system according to claim 22, wherein the platform is configured to measure values of its different sensors at a frequency greater than or equal to 25 Hz.

24. The system according to claim 23, wherein the processor is further configured to process the raw data or the at least one statokinesigram at a first frequency so as to generate re-sampled statokinesigrams at a second frequency, said second frequency having a substantially constant frequency.

* * * * *